United States Patent
Font Pérez et al.

(10) Patent No.: US 9,320,828 B2
(45) Date of Patent: Apr. 26, 2016

(54) THREE-DIMENSIONAL MATRICES OF STRUCTURED POROUS MONETITE FOR TISSUE ENGINEERING AND BONE REGENERATION, AND METHOD OF THE PREPARATION THEREOF

(75) Inventors: Julio Font Pérez, Bizkaia (ES); Maria Begoña Castro Feo, Leioa (ES); Maite Del Olmo Basterrechea, Sopelana (ES); Maria Dolores García Vázquez, Barakaldo (ES); Jorge Rubio Retama, Madrid (ES); Enrique López Cabarcos, Madrid (ES); Carmen Rueda Rodríguez, Madrid (ES); Faleh Tamimi Mariño, Madrid (ES); Mohammad Hamdan Ali Alkhraisat, Madrid (ES)

(73) Assignee: HISTOCELL, S.L., Derio (ES)

( * ) Notice: Subject to any disclaimer, the term of this patent is extended or adjusted under 35 U.S.C. 154(b) by 255 days.

(21) Appl. No.: 13/002,939

(22) PCT Filed: Jul. 8, 2009

(86) PCT No.: PCT/ES2009/000358
§ 371 (c)(1),
(2), (4) Date: Feb. 8, 2011

(87) PCT Pub. No.: WO2010/004066
PCT Pub. Date: Jan. 14, 2010

(65) Prior Publication Data
US 2011/0158963 A1 Jun. 30, 2011

(30) Foreign Application Priority Data
Jul. 8, 2008 (WO) .................. PCT/ES2008/000482

(51) Int. Cl.
*A01N 63/00* (2006.01)
*A61L 27/12* (2006.01)
(Continued)

(52) U.S. Cl.
CPC ............. *A61L 27/12* (2013.01); *A61L 27/3804* (2013.01); *A61L 27/3847* (2013.01); *A61L 27/56* (2013.01); *A61L 27/58* (2013.01); *C01B 25/32* (2013.01);
(Continued)

(58) Field of Classification Search
None
See application file for complete search history.

(56) References Cited

U.S. PATENT DOCUMENTS 6,905,516 B1 * 6/2005 Lemaitre et al. ........... 623/23.56
2003/0006534 A1 * 1/2003 Taboas et al. ................ 264/401
2005/0267593 A1 * 12/2005 Lin et al. .................... 623/23.51

OTHER PUBLICATIONS

Tamimi et al., J Biomed Mater Res 87A: 980-985 (2008).*
(Continued)

*Primary Examiner* — Patricia A Leith
*Assistant Examiner* — Erin M Bowers
(74) *Attorney, Agent, or Firm* — Sughrue Mion, PLLC

(57) ABSTRACT

The present invention is comprised within tissue engineering and, specifically, within bone regeneration. The invention relates to a porous three-dimensional matrix of monetite which is biocompatible, has structured porosity and is predefined and reabsorbable, as well as to the method of synthesis capable of producing said material and the applications thereof. These matrices are a perfect base for cell colonization and proliferation, allowing the application thereof in tissue engineering and bone regeneration as a result of their advantageous properties of biocompatibility, reabsorption, osteoinduction, revascularization, etc.

20 Claims, 28 Drawing Sheets
(4 of 28 Drawing Sheet(s) Filed in Color)

(51) Int. Cl.
*A61L 27/38* (2006.01)
*A61L 27/56* (2006.01)
*A61L 27/58* (2006.01)
*C01B 25/32* (2006.01)
*A61F 2/28* (2006.01)

(52) U.S. Cl.
CPC ................ *A61F 2/28* (2013.01); *A61L 2430/02* (2013.01); *Y10T 428/24744* (2015.01)

(56) References Cited

OTHER PUBLICATIONS

Hutmacher et al., J Tissue Eng Regen Med 1: 245-260 (2007).*
Uwe Gbureck, et al., "Resorbable Dicalcium Phosphate Bone Substitutes Prepared by 3D Powder Printing", Advanced Functional Materials, 2007, pp. 3940-3945, vol. 17.

\* cited by examiner

Fig. 19
a) *TOPVIEW*
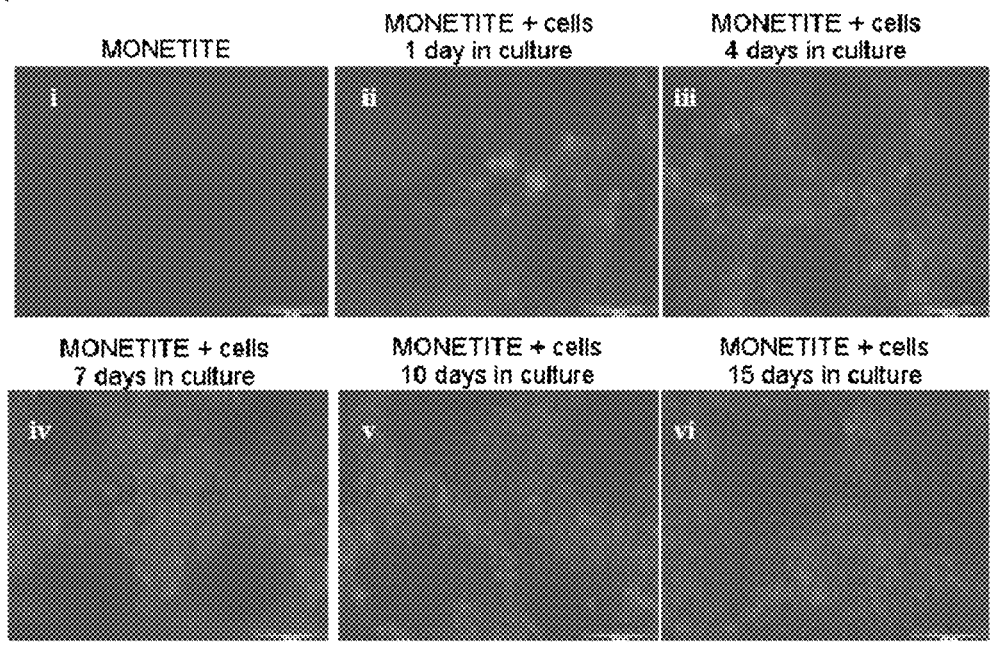
b) *SIDEVIEW*
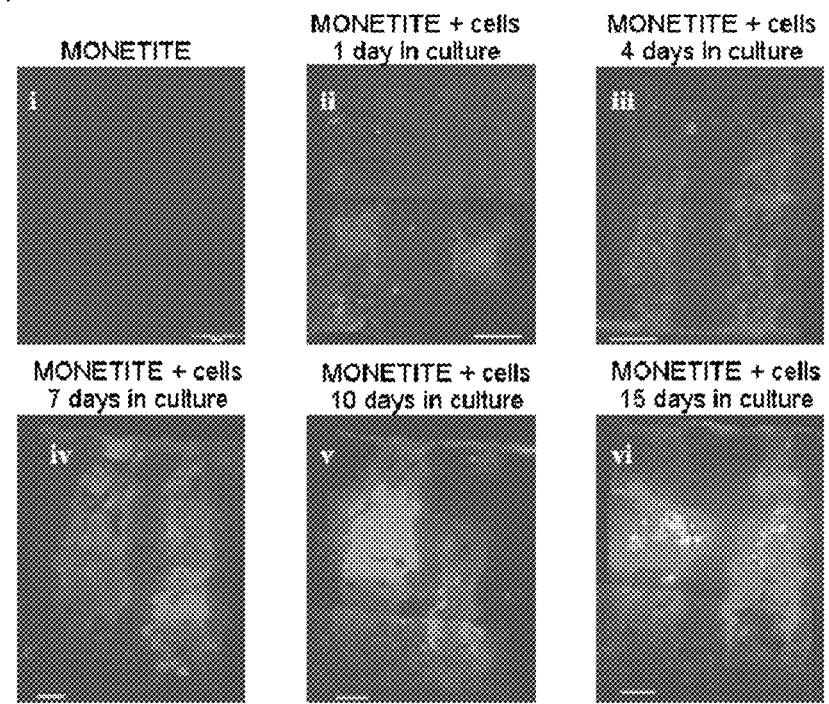

SIDEVIEW

| no. of cells | 0.5x10⁶ | 1x10⁶ | 2x10⁶ | 3x10⁶ | 4x10⁶ |
|---|---|---|---|---|---|
| TGFβ1(pg/ml) | 252±30 | 355±3 | 547±85 | 616±7 | 563±13 |

| Time in culture (days) | 1 | 4 | 7 | 10 | 15 |
|---|---|---|---|---|---|
| TGFβ1(pg/ml) | 550±8 | 1862±131 | 1474±31 | 969±30 | 1327±15 |

| no. of cells | 0.5x10⁶ | 1x10⁶ | 2x10⁶ | 3x10⁶ | 4x10⁶ | 5x10⁶ |
|---|---|---|---|---|---|---|
| TGFB1(pg/ml) | 159±8 | 158±14 | 214±2 | 289±14 | 295±7 | 260±8 |

| Time in culture (days) | 1 | 4 | 7 | 10 | 15 |
|---|---|---|---|---|---|
| TGFB1(pg/ml) | 92±35 | 223±7 | 243±24 | 336±7 | 281±20 |

THREE-DIMENSIONAL MATRICES OF STRUCTURED POROUS MONETITE FOR TISSUE ENGINEERING AND BONE REGENERATION, AND METHOD OF THE PREPARATION THEREOF

This is a National Stage of International Application No. PCT/ES2009/000358 filed Jul. 8, 2009, claiming priority based on International Application No. PCT/ES2008/000482 filed Jul. 8, 2008, the contents of all of which are incorporated herein by reference in their entirety.

FIELD OF THE INVENTION

The present invention is comprised within tissue engineering and, specifically, within bone regeneration. The invention relates to a porous three-dimensional matrix of monetite which is biocompatible, has structured porosity and is pre-defined and reabsorbable, as well as to the method of synthesis capable of producing said material and to the applications thereof. These matrices are a perfect base for cell colonization and proliferation, allowing the application thereof in tissue engineering and bone regeneration as a result of their advantageous properties of biocompatibility, reabsorption, osteoinduction, revascularization, etc.

BACKGROUND OF THE INVENTION

The loss of bone mass and quality is a serious health problem which is even more common in elderly patients.

The success in the regeneration of a bone defect using three-dimensional materials, which are initially colonized by progenitor cells in vitro, depends to a great extent on the characteristics and structure of the material.

Biomaterials have been used for almost a century to repair or replace bone segments of the musculoskeletal system.

The use of autogenous bone grafts, i.e., from the individual himself, is a widely used method for filling bone cavities and for surgical reconstructions. However, there is a limited bone supply and the patient must furthermore be subjected to additional trauma in order to obtain the graft. Another option is donor allografts which also have drawbacks such as a slower neoformation rate, lower osteogenic capacity, reabsorption rate, lower revascularization as well as a higher risk of immunogenic response and transmission of pathogenic agents.

It is ideal to obtain a material similar to bone, which is biocompatible, does not present adverse biological reactions, is reabsorbable and is gradually degraded as the new tissue is formed, thus progressively transferring the loads to the new bone, preventing a second surgical intervention for removing the implant. A material the degradation products of which are easy to eliminate and non-toxic, which is osteoinductive and induces bone tissue formation is also ideal.

In the organism, bone degradation and reabsorption are carried out by osteoclasts. They are cells derived from monocytes which are fixed to the surface of the bone. Once fixed, they start releasing protons to the exterior, for the purpose of lowering the pH of the external medium. With this acidic environment, the hydroxyapatite crystals forming part of the mineral component of bone are solubilized. The hydroxyapatite of bone is solubilized in amorphous calcium phosphate particles, which are eliminated by macrophages, or in $Ca^{2+}$ and $PO_4^{3-}$ ions which accumulate in the extracellular fluid. These ions diffuse towards the blood capillaries, entering the systemic circulation to be eliminated by urine through the kidney. These released ions can also be reused by osteoblasts to form new bone. Osteoclasts are also in charge of the degradation of the organic phase of bone by means of enzymatic processes.

The research in new biomaterials for bone repair attempts to reduce the need for bone grafts as much as possible, seeking an artificial substitute which over time is reabsorbed and/or is integrated with the adjacent bone and furthermore serves as fixing in osteoporotic fractures. The mechanical properties of the bone substitute must be as similar as possible to those of spongy bone. The material must furthermore aid in the stability of the fracture and be resistant enough to decrease the necessary external support or immobilization time. Said material must be reabsorbable, biocompatible and osteoinductive, i.e., it must attract mesenchymal cells and other cell types located close to the implant and favor the differentiation thereof into osteoblasts, and also osteoconductive, i.e., it mist act as a mold for the formation of new bone.

Seeking a similarity with what occurs in the organism, the non-reabsorbable materials used up until now are being substituted in bone implants with reabsorbable materials. These biomaterials do not interfere in the development and growth of the new bone formed, since they are gradually replaced by host tissue. Furthermore, they have a higher biocompatibility, they participate naturally in bone reconstruction and it is not necessary to remove them by means of surgery, after bone regeneration. These materials have to remain for the sufficient time for correct bone regeneration to take place and disintegrate gradually without harming the patient and without intervening in the correct development and growth of the bone.

The biomaterials which set forming a mineral calcium phosphate are especially interesting in bone regeneration since they resemble the mineral phase of natural bone and are susceptible of bone remodeling and of reabsorption due to their metastable crystal structure.

The reabsorbable materials which are being used as bone substitutes include calcium phosphates; hydroxyapatite (HAP), tricalcium phosphate (B-TCP) and dicalcium phosphate dihydrate (DCPD) (Stubbs et al., 2004; Schnettler et al., 2004). These materials have an excellent biocompatibility due to their chemical and crystalline similarity to the mineral component of bone, but have difficulties in relation to solubility and reabsorption capacity in vivo.

Hydroxyapatite (HAP) has been one of those which has aroused the greatest interest. This material is per se the inorganic phase from which bones are formed and it has therefore been widely used in bone regeneration. An example of this are some commercial products such as Interpore 200® Interpore 500®, Cerasorb® and Collagraft®. However, and due to the fact that it has one of the most stable crystal structures, the material has a slow reabsorption.

HAP is the material having the highest biocompatibility, as it is the most similar one to the crystals formed by bone, but it is not reabsorbable in vivo. The degradation of this material occurs by contact with solutions with a low pH and by phagocytosis. By means of dissolution the amorphous calcium phosphate particles are released, and can be eliminated by macrophages by phagocytosis or be embedded in the new bone formed. Macrophages can dissolve these particles and restore Ca and P to the pool of the organism (Frayssinet et al., 1999; Benahmed et al., 1996). However, it has not been observed that these particles give rise to osteoclast activation (Frayssinet et al., 1999).

All the studies conducted corroborate the resistance of this material to degradation once it is implanted in the organism, due to its poor solubility at physiological pHs. Implants of this type in animals are reabsorbed by 5.4% in 6 months compared to those based on B-TCP, which are reabsorbed by 85%. (Eggli et al., 1988).

In humans, the implants made with Bio-Oss (HAP) are considered as non-reabsorbable, since the studies conducted demonstrate that between 3-6 years are needed for them to be reabsorbed due to osteoclast activity (Taylor et al., 2002). The presence of this material in the organism for so much time can interfere in the bone remodeling process, as well as in the osseointegration capacity (Affe et al., 2005; De Boever 2005).

As a result, this material has traditionally been used in mixtures with organic material as polymers to increase the reabsorption thereof. Examples of these applications are described in U.S. Pat. No. 5,866,155, which describes the incorporation of hydroxyapatite in polylactic matrices, or in U.S. Pat. No. 5,741,329, which is a variation of U.S. Pat. No. 5,866,155 which intends to correct several defects derived from the local acidification of the medium after incorporating cements in the organism.

To that end, for the purpose of improving the capacity of reabsorption of calcium phosphates and increasing their osteoconductive capacity, crystalline calcium phosphate phases less stable than hydroxyapatite 6, such as B-TCP and DCPD (Brushite), having better solubility and reabsorption in vivo, have been used in recent years.

B-TCP has more osteoconductivity and a better reabsorption than HAP (Franco et al., 2006). It is considered as a moderately reabsorbable material, in in vivo studies it has been observed that at least one year is needed for its reabsorption in animals and from 6 to 8 months in humans (Wiltfang et al., 2003; Suba et al., 2004). Its degradation increases calcium deposits and this is associated with a higher alkaline phosphatase activity, which enzyme is involved in bone formation (Trisi et al., 2003; Sugawara et al., 2004).

DCPD is also biocompatible, osteoconductive and the most reabsorbable due to being the most soluble at physiological pHs. This allows new bone to be formed more quickly. It is biodegraded in physiological environments and it is reabsorbed by adjacent cells (Tris et al., 2003). It is proved to be reabsorbed in vivo up to three times quicker than HAP and B-TCP (Herron et al., 2003; Chow et al., 2003; Tas & Bhaduri 2004; Tamini et al., 2006).

Studies suggest that part of the DPDC material can be converted into HAP after its implantation, which can delay the elimination of the implant by osteoclasts by several weeks (Constanz et al., 1998). This conversion can make the cells acidify the medium and make the biocompatibility of the material decrease together with a reduction in its reabsorption. The addition of Mg and Ca (calcium carbonate) salts or the combination thereof with BTCP can prevent this conversion.

Using this material it is observed that generation of bone and elimination of the material occur in a balanced manner after the $4^{th}$ week (Fallet et al., 2006) and the $8^{th}$ week post-intervention (Constanz et al., 1998). This is important because if the degradation were greater than the synthesis instability and inflammatory reactions would be created.

Thus, among these calcium phosphates, brushite (DPCD) is one of the materials of greatest interest in bone regeneration. Due to the interesting properties thereof, there are currently brushite cements designed for setting in situ. Thus, for example, U.S. Pat. No. 6,733,582 and US2006213398 claim brushite cements with in situ setting, Chronoss Inject® being an already marketed product of this type. However, this material has a great problem when it is sterilized since it decomposes when it is heated, which makes its appropriate sterilization difficult.

The state of the art contemplates different publications relating to the sterilization of cements which can be used as bone material substitutes, as well as about the methods used to make said matrices and their sterilization. However, as reflected in patent application JP2004018459, when said cements are sterilized by autoclave, the characteristics of said cements are altered, translating into obtaining bone mineral substitutes which do not meet the characteristics necessary for their use in bone regeneration in terms of reabsorption, stability and colonization and other essential properties.

As occurs with DPCD, Monetite is reabsorbed in vivo in a similar time and manner. It is gradually dissolved at physiological pHs in the extracellular tissues surrounding the implant and the actual cells colonizing it (endothelial cells, osteoclasts, osteoblasts, macrophages . . . ) would be responsible for the elimination or reuse thereof as occurs in bone.

Documents such as US20060263443 present Monetite, dicalcium phosphate anhydrous (DCPA), obtained by dehydration of Brushite, in combination with other calcium phosphate biomaterials. Due to the combination, the sterilization results were not acceptable for using these materials in implants and bone regeneration. Additionally, these materials are reaction intermediates and not structures with their own capacity to be used in the technical field of bone regeneration.

Additionally, for correct bone regeneration, it is necessary for the biomaterial to have a suitable porosity allowing cell colonization and proliferation, vascularization, increase of the surface of contact and therefore increase of the surface of interaction with the host tissue which allows the acceleration of bone regeneration. These characteristics must be accompanied by a correct reabsorption rate providing the cells with the time necessary for regeneration.

Thus, Gbureck, Uwe et al., 2007, relate to Brushite and Monetite implants prepared by means of the three-dimensional printing technique. To achieve said implants, matrices of brushite which are hydrothermally dehydrated, being transformed into Monetite, are obtained first. However, Table 2 of said article shows that the calcium phosphate material defined as Monetite in said article only has a Monetite content of 63%, not specifying the size or the distribution of its porosity, having a destructured porosity. Thus, said structures are not valid for the purposes of the present invention.

U.S. Pat No. 6605516 presents bone substitutes with a controlled anatomical shape which adjust exactly to the morphology of the injury. Said substitutes are formed by chemically consolidated calcium phosphate cement materials. The invention also relates to porogenic phases and molds which allow obtaining calcium phosphates with macroporous architectures and external geometries by means of using said molds. However, in its particular embodiments, the invention presents Brushite materials, not presenting Monetite materials and the macroporous structures presented therein also not being valid for the object of the present invention. Thus, the present invention provides matrices of monetite (metastable calcium phosphate phase of monetite), with a high thermal stability which allows sterilizing the material by means of autoclaving, thus simplifying the sterilization processes and which, furthermore, due to its specific structural arrangement of pores, which arrangement is obtained as a result of a specific design of the material, involves an improvement of the osteoinductive capacity of materials proposed by the state of the art since it is synthesized in the form of a porous block with defined structured macroporosity characteristics, increasing the specific surface area, as well as the area of contact with the osteoblasts and facilitating the nutrient transport processes for cells, a crucial factor for bone generation, all of this together with the high capacity of reabsorption thereof in the suitable time period for the adjacent cells to colonize the material and be able to replace the reabsorbed material with physiological bone matrix.

The in vitro degradation of the matrices of the invention does not affect cell proliferation and they are furthermore bioactive, non-cytotoxic, non-mutagenic and hemocompatible.

DESCRIPTION OF THE INVENTION

In order for a biomaterial to be able to give rise to a stable bone regeneration, the cells of the implant area, osteoblasts from the adjacent bone, mesenchymal stem cells from bone marrow and endothelial cells from the systemic circulation must be capable of simultaneously and homogeneously colonizing the biomaterial. This will allow the formation of a new physiological bone matrix as the biomaterial is gradually resorbed and the development of a new vascular system, which will provide the blood supply necessary for the survival of the new tissue.

An important property to be taken into account in relation to this aspect is the porous structure, because it affects both the biodegradability, the higher the degree of porosity the better the reabsorption, and cell colonization. The materials must have pore sizes and interconnections allowing the colonization of both endothelial cells (for the formation of new blood vessels) and of bone cells. Furthermore, the microporous and interconnected nature, which allows the diffusion of nutrients and gases and also of the typical metabolites of cell activity. Bone is not a compact material but rather it has different porosities intercommunicated with one another. Systems of interconnected pores communicate solid (cortical) bone with spongy (trabecular) bone (FIG. 16). These porosities range from 100-150 µm in cortical bone to 500-600 µm in spongy bone.

The present invention presents a new tissue engineering system, intended to regenerate the bone structure by tackling a curative strategy instead of a merely reparative strategy. Said regeneration is applicable for osteoporosis.

Tissue engineering is considered as a discipline improving, maintaining and repairing pathologies in organs and in tissues. The creation of a system based on tissue engineering involves the integration of viable cells, a biocompatible material designed especially for a biomedical application and signaling molecules regulating the cell activities required at all times of the treatment.

Thus, the present invention provides matrices with a geometry of non-random, i.e., ordered or predefined porosity, formed by monetite, in the design of which the porosities of bone have been taken into account, so that neovascularization and cell colonization take place. Said material is presented sterilized, ready for its use and as a result of its specific design, it achieves a specific structural arrangement of pores, i.e., a spatial arrangement and spatial configuration of previously established and induced ordered porosity, which involves an improvement of the osteoinductive capacity compared to other calcium phosphates, including other combinations of calcium phosphate which include monetite.

Said matrices are obtained in the form of a porous block with defined macro-, meso- and microporosity characteristics which increase the specific surface area, as well as the area of contact with the osteoblasts, facilitating the nutrient transport processes for cells, a crucial factor for bone generation.

The design of these matrices of monetite of the invention has taken into account the characteristic porosities of natural bone, which porosities allow neovascularization and cell colonization.

The new matrices of the invention are formed by the biomaterial Monetite, a dehydrated DPCD (DPC), suitable for bone regeneration. Said matrices are formed by at least 95%±5% monetite, preferably by 95% monetite and more preferably by 100% monetite. The traces of material correspond to beta-tetracalcium phosphate. The in vitro degradation of this material does not affect cell proliferation and it is furthermore bioactive, non-cytotoxic, non-mutagenic and hemocompatible as shown in Example 4.

As a result of their design and composition, the matrices of the invention are reabsorbed in the suitable time period for the adjacent cells to colonize the material and be able to replace the reabsorbed material with physiological bone matrix.

Matrix relates to any three-dimensional structure useful in bone regeneration which allows the cell growth and proliferation of the cells invading it.

Cells are understood as:
  adult mesenchymal stem cells preferably derived from adipose tissue, but they can also be from bone marrow or any other location which has proved to be a source of these cells. These cells can be used differentiated into the osteoblastic or endothelial strain.
  Osteoblasts obtained from bone fragments.
  Endothelial cells.
  Combinations of adult mesenchymal stem cells that are undifferentiated or differentiated into the osteoblastic or endothelial strain, osteoblasts, osteoclasts, osteocytes from bone and endothelial cells.

Macropores: when the pores have diameters greater than or equal to 100 microns.

Mesopores: when the pores have diameters less than 100 microns but greater than or equal to 10 microns.

Micropores: When the pores have a diameter less than 10 microns.

Amorphous matrix: A matrix having a geometry of random, non-ordered and non-predefined porosity, which does not follow a spatial distribution and spatial configuration of ordered and previously established porosity, regardless of whether said porosity is natural (intrinsic to the material) or induced.

Structured matrix or matrix with structured porosity: A matrix having a geometry of non-random, ordered or predefined porosity, having a spatial distribution and spatial configuration of previously established and induced ordered porosity. The matrices of the present invention are matrices with structured porosity with a predefined porosity which confers to them a series of ideal properties for their use in bone regeneration.

Osteoinduction: bone neoformation by apposition to the material, forming a framework for cell proliferation with osteoblastic activity, forming new bone. It is the act or process of stimulating osteogenesis.

Osteogenesis: generation or development of bone tissue, through the differentiation of mesenchymal cells into osteoblasts.

Bone regeneration: formation of new bone which, after a remodeling process, is identical to the pre-existing bone. In bone regeneration, a response is generated in which blood vessels, cells and the extracellular matrix are involved. The biomaterial of the invention is applicable in tissue engineering and bone regeneration and, therefore, can be used in the treatment of the following bone pathologies:
  Hypertrophic and non-hypertrophic pseudarthrosis
  Osteonecrosis
  Osteoporosis
  Bone defects caused after the removal of a prosthesis, extirpation of a tumor, by biochemical and metabolic disorders or congenital diseases.
  Treatment of injuries and traumas
  Treatment of bone fractures Any pathology in which it is necessary to repair bone tissue.

Treatment of maxillofacial bone defects.

Bone augmentation prior to the application of dental implants

Cell colonization: capacity of the cells to expand on the biomaterial, being capable of proliferating and increasing the cell population until invading the entire matrix. A measurement of the capacity to colonize a matrix is the analysis of the number of cells on the biomaterial over time (data of the proliferation graph).

Cell adhesion: capacity of the cells to bind to other cells or to a matrix. Adhesion can occur by specific interactions such as electrostatic forces and is regulated by specific proteins referred to as adhesion molecules. The capacity to adhere to a biomaterial can be analyzed by means of viewing the cells arranged on the biomaterial under a microscope. The surface of contact between the cells and biomaterial will be a representative measurement of the affinity of the cells for that biomaterial.

In a first aspect, the present invention relates to biocompatible three-dimensional matrices with structured porosity formed by porous monetite, hereinafter matrices of the invention, comprising three-dimensional matrices of monetite with structured porosity, corresponding to cylindrical macropores of between 350-650 µm in diameter, uniformly separated from another by between 0.4-0.6 mm. Said monetite has the intrinsic porosity of the material, on which the indicated structured macroporosity is induced.

In the matrices of the invention, said structured porosity is distributed in the maximum area of the matrix allowing said matrix to stably maintain its mechanical stability. In a particular embodiment, said maximum area is the area remaining after eliminating the outer perimetric area of the matrix, ranging between 0.1 and 0.9 mm in width, preferably 0.5 mm in width.

Thus, the materials which are used in osteogenesis must imitate the morphology, structure and function of the bone to achieve a correct integration in the host tissue.

It has been proved that the structure determined by the porosity and the pore diameter of the materials used in bone regeneration affect bone formation both in vitro and in vivo. The pores are necessary for bone tissue formation to occur, since they allow the migration and the proliferation of osteoblasts and mesenchymal cells and also vascularization. Thus, the material of the invention provides the conditions necessary for achieving correct bone regeneration as a result of its porosity characteristics which allow the colonization and proliferation of the cell types necessary for such effect.

In vitro results carried out with matrices of other materials show that a low porosity stimulates osteogenesis since cell aggregation occurs, which suppresses proliferation by stimulating osteogenesis. These same experiments show that a high porosity does not affect cell adhesion but does increase proliferation since there is an increase of the surface of contact and the transport of oxygen and nutrients is also facilitated (Takahashi et al., 2004). According to these results, osteogenesis is not affected by the pore size but it does increase with a low number of pores.

In addition, in vivo, an integration and penetration of the cells in the material as well as the vascularization thereof are required for it to be incorporated to the tissue of the individual. A high porosity and pore size such as those provided by the matrices of the invention facilitate these requirements.

Initially, according to first studies the minimum diameter required for bone formation was considered to be about 100 µm for the cell migration and transport processes to be carried out. However, diameters greater than 300 µm are currently proposed since the presence of these macropores increases bone formation due to the fact that they allow capillary formation therein. Vascularization affects the development of osteogenesis. Pores with small diameters favor hypoxic conditions and do not induce osteogenesis but rather chondrogenesis.

Thus, long and large tunnel-shaped pores of the matrix of the invention allow the vascularization thereof and the development of osteogenesis.

Furthermore, the pores with large diameters increase the surface of contact, which also increases the surface of interaction with the host tissue, which will accelerate the degradation performed by macrophages.

In the case of amorphous matrices, which have a geometry of random porosity, the vascular network which may be formed is irregular in the structure of the biomaterial and will not be able to connect with the vascular network of the bone, such that the implant will not be able to be effectively integrated with the tissue of the recipient.

However, the porosity structure adopted by the matrices of the present invention takes into account the incorporation of pores with the suitable size for the co-existence of the required cell species and for the formation of a bone and vascular frame in the entire implant and furthermore for the connection with the recipient area to be allowed, so that tissue integration can take place.

The new design incorporates cylindrical-shaped (tunnel-shaped) 350 µm-650 µm macropores completely traversing the structure of the material for a suitable cell colonization (in terms of different cell types and a sufficient number of each type) of the cells of the adjacent tissues, as well as an integration with the recipient tissue. Furthermore, in the entire structure it contains a network of micropores for a sufficient diffusion of nutrients, gases and waste products of cell metabolism.

As can be observed in FIG. 13, the advantage in terms of the cell colonization of the matrices of the invention can be shown in direct studies for cell viewing under a scanning electron microscope. However, as shown in FIG. 14, the amorphous biomaterials, which show a destructured and non-predefined distribution of macropores, produced in the process for obtaining the cement of the present invention, have pores which do not connect the internal structure. In other words, the number of macropores is insufficient and their distribution is unsuitable for a suitable colonization of the cells to take place, such cells being for the most part relegated to the surface of the material.

The success in the process for forming a new bone is directly related to the amount of bone-forming cells involved in the process, as well as in the formation of a consistent vascular network over the entire biomaterial. Thus, as shown in FIG. 14, the matrices of material with structured porosity of the invention, which have an ordered, induced and previously established spatial distribution and spatial configuration of macropores, allow an extensive cell colonization over the entire biomaterial, a greater diffusion of nutrients and of signaling molecules which will determine cell behavior.

Therefore, the matrices of the invention, with a high percentage of porosity, especially of macroporosity, in which there are pores with large diameters (>300 µm, specifically between 350 and 650 µm, and preferably 500±60 µm) and in the form of continuous tunnels, will increase the osseointegration of the implant after surgery.

In a second aspect, the present invention relates to the method of synthesis of the matrices of the invention, which comprises forming a matrix of monetite with structured porosity which comprises:

Forming a solid phase, corresponding to a porous matrix of brushite by means of the combined use of pore-inducing agents, retarder and mechanical methods during the setting reaction between an acidic calcium phosphate and a basic calcium phosphate.

Mixing the solid phase with distilled water to give rise to the liquid phase

Applying in the cement obtained in step 2 one or more molds, one of them with cylindrical punches, having a diameter of between 350 and 650 µm, and more preferably 500 µm±60 µm, during the setting to generate in the matrices vertical cylindrical pores of between 350 and 650 µm, and more preferably 500 µm±60 µm in diameter separated by a distance of between 0.4-0.6 mm and more preferably separated by a distance of 0.5 mm±60 µm.

Sterilizing the porous brushite and heat-transforming it into a porous monetite.

Specifically, in the method of synthesis used, the product obtained in step 1 gives rise to a solid phase which is mixed with distilled water to give rise to a liquid phase. As a preferred embodiment, the invention proposes using beta-tricalcium phosphate as basic calcium phosphate, and calcium monophosphate as acidic phosphate.

According to the invention, to carry out the mixing, the molar ratio of basic phosphate/acidic phosphate is 1.6-1.8 for a time of approximately 10 minutes, the concentration of pore-inducing agent is 1-20% by weight and that of retarder is between 0.4-0.6% by weight; preferably a molar ratio of basic phosphate/acidic phosphate of 1.785, a concentration of pore-inducing agents 3-10% by weight and that of retarder is 0.54% by weight.

The molar ratio of basic phosphate/acidic phosphate to carry out the mixing is 1.6-1.8, preferably 1.785, for a time of approximately 10 minutes. Calcium carbonate is added at concentrations between 1-20% by weight, preferably between 3-100. As a retarder of the setting reaction, the invention proposes using sodium pyrophosphate in a proportion of 0.4-0.6 by weight, 0.54% being the preferential option.

This solid phase thus obtained is mixed with the liquid phase (distilled water) in a (P/L) ratio of 3.

With respect to acidic and basic calcium phosphates, pore-inducing agents and retarders to be used in the invention, the person skilled in the art knows the different possible compounds and combinations to be used.

Molds which allow obtaining the matrices of the invention, which have the structured distribution of pores indicated above, are filled with the paste obtained.

The mold of the invention used to develop the biomaterial relates to any mold having cylindrical punches, the base of which has a diameter of between 350 and 650 µm, and which are separated from one another by between 0.4 and 0.6 mm. Said mold can be constructed in silicone, metal, resistant plastic material or any type of material allowing it to be applied in its use.

The mold can have any desired shape, depending on the shape and size required to repair a particular bone defect for each patient, the biomaterial obtained always maintaining the typical porosity characteristics of the biomaterial of the invention, i.e., cylindrical macropores of between 350 and 650 µm in diameter, more preferably 500 µm±60 µm in diameter, uniformly separated from another by between 0.4 and 0.6 mm, more preferably 0.5 mm±60 µm, in addition to the intrinsic porosity of the biomaterial.

Said molds allow obtaining the matrices of the invention, in which the structured porosity is distributed in the maximum area of the matrix allowing said matrix to stably maintain its mechanical stability.

In a particular embodiment, said molds allow obtaining matrices in which the maximum area in which the structured porosity is distributed is the area remaining after eliminating the external perimetric area of the matrix, between 0.1 and 0.9 mm in width, preferably 0.5 mm in width.

The invention also contemplates using more than one mold:

A first mold which allows obtaining the matrices of monetite in the desired shape but without the structured porosity A second mold which in a planar surface has cylindrical punches, with a diameter of between 350 and 650 µm, preferably 500 µm±60 µm, and which are separated from one another by between 0.4 and 0.6 mm, preferably 500 µm±60 µm. Said second mold must be applied after removing the first mold, introducing therein the parts obtained with the first mold. The second mold is covered with a lid as shown in FIG. 1c.

Thus, the biomaterial of the invention can be presented in the form of pellets, sheets, cylinders, etc., and any other form which is useful for repairing a particular bone defect of a patient.

In a preferred aspect of the invention, the mold is in the form of a pellet or cylinder with a diameter between 2 and 50 mm, preferably between 2 and 15 mm, and a height between 1 and 50 mm, preferably between 1 and 5 mm, and more preferably:

with a diameter of 10 mm and a height of 3 to 5 mm, preferably 3 or 5 mm, having 64 punches, or with a diameter of 8 mm and a height of 3 to 5 mm, preferably 3 or 5 mm, having 39 punches, or with a diameter of 7 mm and a height of 3 to 5 mm, preferably 3 or 5 mm, having 28 punches, or with a diameter of 5 mm and a height of 3 mm, having 12 punches In all the cases, the punches are cylindrical with a diameter of 500 µm±60 µm, separated from one another by 500 µm±60 µm, and distributed respecting a perimetric area of 5 mm (taken from the edge of the pellet) free of punches.

One minute after starting the setting of the cement, the latter is placed for approximately 30 minutes in the mold, before its solidification ends, and it is removed, the pores determined by the mold having been formed. Once it has set completely, the matrix of brushite formed is subjected to autoclaving between 120 and 130° C. for 24-25 minutes, its conversion into Monetite, completely sterilized and suitable for use, occurring.

In another preferred aspect of the invention, a first mold is made of silicone and has cylindrical cavities for pellets or cylinders of the size of the matrices of the invention which are to be manufactured. In a particular embodiment of the invention, said cavities have a diameter between 2 and 50 mm, preferably between 2 and 15 mm, and a height between 1 and 50 mm, preferably between 1 and 5 mm, and more preferably:

a diameter of 10 mm and a height of 3 to 5 mm, preferably 3 or 5 mm, a diameter of 8 mm and a height of 3 to 5 mm, preferably 3 or 5 mm, a diameter of 7 mm and a height of 3 to 5 mm, preferably 3 or 5 mm, a diameter of 5 mm and a height of 3 mm, Said molds are not involved in the formation of the macropores.

In this aspect of the invention, the second mold is metallic, it has the dimension of each of the previous parts, and at its base it has, uniformly distributed, 500 microns±60 μm cylindrical punches, separated from one another by 500 microns±60 μm, which give rise to the macroporous component of the matrices of monetite, distributed respecting a minimum perimetric area of 0.5 mm (taken from the edge of the pellet) free of punches. In a particular embodiment, said metallic molds have a diameter between 2 and 50 mm, preferably between 2 and 15 mm, and a height between 1 and 50 mm, preferably between 1 and 5 mm, and more preferably:

- a diameter of 10 mm and a height of 3 to 5 mm, preferably 3 or 5 mm, and 64 punches or
- a diameter of 8 mm and a height of 3 to 5 mm, preferably 3 or 5 mm, and 39 punches or
- a diameter of 7 mm and a height of 3 to 5 mm, preferably 3 or 5 mm, and 28 punches or
- a diameter of 5 mm and a height of 3 mm, and 12 punches in all the cases respecting a minimum perimetric area of 0.5 mm (taken from the edge of the cylinder) free of punches.

In this case, the process is identical to the previous one, with the difference that immediately after mixing the solid phase and the liquid phase, the first silicone mold is filled. Before the biomaterial ends its setting, the parts are removed from the silicone mold. The parts are subsequently introduced in the metallic mold with punches (being covered with the metallic lid according to FIG. 1c), until the setting ends in a water bath at 37° C. for 30 minutes. Once solidified, they are removed from the metallic mold obtaining the cylindrical parts with the determined porosity. The matrices formed are subjected to autoclaving between 120 and 130° C. for 24-25 minutes, their conversion into Monetite, completely sterilized and suitable for use, occurring. The use of these molds gives rise to monetite pellets with structured porosity. In a particular embodiment, said pellets have a diameter between 2 and 50 mm, preferably between 2 and 15 mm, and a height between 1 and 50 mm, preferably between 1 and 5 mm, and more preferably:

- a diameter of 10 mm and a height of 3 to 5 mm, preferably 3 mm or 5 mm, having a uniform distribution of 64 macropores with a diameter of 500 μm±60 μm, separated from one another by 500 μm±60 μm.
- a diameter of 8 mm and a height of 3 to 5 mm, preferably 3 mm or 5 mm, having 39 macropores with a diameter of 500 μm±60 μm, separated from another by 500 μm±60 μm.
- a diameter of 7 mm and a height of 3 to 5 mm, preferably 3 mm or 5 mm having 28 macropores with a diameter of 500 μm±60 μm, separated from one another by 500 μm±60 μm.
- a diameter of 05 mm and a height of 0.3 mm having 12 macropores with a diameter of 500 μm±60 μm, separated from one another by 500 μm±60 μm.

In all the cases, the monetite pellets have a minimum perimetric area of 0.5 mm (taken from the edge of the pellet) free of macropores which allows them to maintain the conditions of mechanical stability and strength necessary to be used in their applications.

Thus, the final distribution of macropores in said pellets respects both the minimum perimetric area of 0.5 mm free of macropores, as well as the size and distance between pores (as described above).

The products of the present invention are applicable in the field of tissue engineering and bone regeneration. Thus the matrices of monetite of the invention, obtained through the defined molds are applicable for cell support and growth and the applications defined above.

In a particular embodiment, the pellets of the invention are applied in the form of several units (as an assembly of parts), being arranged such that they adapt completely to the space of the bone defect, facilitating the homogeneous entrance of nutrients, gases and cells in the entire area to be repaired, facilitating recovery thereof as a result of said arrangement and preventing the occurrence of necrotic areas.

In a preferred aspect, the invention relates to the use of the matrices of the invention as a growth support for mesenchymal cells of different origins, including adipose origin, osteoblasts, endothelial cells and combinations of adult mesenchymal stem cells that are undifferentiated or differentiated into the osteoblastic or endothelial strain, osteoblasts, osteoclasts, osteocytes from bone and endothelial cells, for their use in bone regeneration.

The matrices of Monetite with structured porosity of the invention are reabsorbed in vivo in a longer time and in a similar manner with respect to DCPD, preventing the drawback of their transformation into HA (as shown by Example 10 which compares the matrices with structured porosity of the invention against matrices of brushite made with the structured porosity of the matrices of the present invention). Thus, said matrices will gradually be dissolved at physiological pHs in the extracellular tissues surrounding the implant and the actual cells colonizing them (endothelial cells, osteoclasts, osteoblasts, macrophages . . . ) will be responsible for the elimination or reuse thereof as occurs in bone. Furthermore, their combination with calcium carbonate in the process for obtaining them prevents their transformation into HAP.

As occurs with DPCD, the reabsorption thereof starts between the $4^{th}$ and $8^{th}$ week, a time period which is suitable for the adjacent cells to colonize the material and be able to replace the reabsorbed material with physiological bone matrix. This biodegradability is adjusted to what occurs in the organism, wherein the bone growth in the defects can take place in a time period comprised between 2 and 6 months, depending on the type of bone and on the size of the defect (Francone V. 2004).

In addition to the biodegradability, other properties such as the roughness and texture of the material of the invention have been taken into account in the study of the matrices. Thus, according to the biological tests conducted on the matrices of porous monetite with structured macroporosity of the invention, an adhesion to the material greater than 95% is demonstrated, where the cells do not change their morphology in contact with the material and colonize the entire surface, communicating with one another as in any functional tissue.

It must be taken into account that monetite can show very low resistance and elasticity with respect to that of trabecular bone (elasticity 50-100 MPa and compression 5-10 MPa). However, it would be almost impossible to equal the mechanical properties of bone. And it has been demonstrated that it is enough for the material to reach mechanical properties sufficient to support cell growth, since when the cells invade the material, they will form the organic phase of the implant and the mechanical properties will improve. The matrices of porous monetite of the invention meet with this requirement.

The monetite material is reabsorbable, bioactive, and has characteristics similar to bone. This material allows cell growth both on its surface and inside it, once in the bone defect it will allow the cells (endothelial cells, osteoblasts, osteoclasts . . . ) to form the necessary scaffold which will be connected to the healthy bone. Subsequently, the monetite will gradually be eliminated little by little, without undergoing transformation into hydroxyapatite, due to the action of osteoclasts, and the osteoblasts will gradually synthesize the new mineral phase which will gradually substitute the monetite, completely eliminating the initial defect.

Thus, a first object of invention relates to a three-dimensional matrix of monetite with structured porosity characterized by having in its structure vertical cylindrical macropores of between 350 and 650 μm in diameter, which longitudinally traverse the matrix from one end to the other, there being a separation of between 0.4-0.6 mm between each macropore. In a particular embodiment, the diameter of the macropores is preferably 500 μm±60 μm. In another particular embodiment, the separation between macropores is preferably 500 μm±60 μm.

Another object of the invention relates to the matrix of monetite with structured porosity the monetite content of which is at least 90%, preferably 95% and more preferably 100%.

A following object of the invention is formed by the matrices of monetite with structure porosity characterized by being obtained by heat-transforming a precursor material. In a particular embodiment, said precursor material which is heat-transformed into monetite consists of a mixture of a solid phase formed by basic calcium phosphates, acidic calcium phosphates, a pore-inducing agent and a retarder which is set by adding distilled water. In another particular embodiment, the molar ratio of basic phosphate/acidic phosphate is 1.6-1.8, the concentration of pore-inducing agent is 1-20% by weight, that of retarder is between 0.4-0.6% by weight and the (P/L) proportion is 3. In another particular embodiment, the molar ratio of basic phosphate/acidic phosphate is 1.785, the concentration of pore-inducing agent is 3-10% by weight and that of retarder is 0.54% by weight. In another particular embodiment, the acidic calcium phosphate is monocalcium phosphate, the basic calcium phosphate is beta-tricalcium phosphate, the pore-inducing agent is calcium carbonate and the retarder is sodium pyrophosphate. In another particular embodiment, the precursor material is Brushite.

Another object of the invention is formed by the three-dimensional matrices of monetite with structured porosity according to the previous claims characterized in that they can adopt any type of shape required to repair a particular bone or tissue defect. In a particular embodiment, said matrix consists of a cylinder with a base diameter between 2 and 50 mm and with a height between 1 and 50 mm. In another particular embodiment, said cylinder has a base diameter between 2 and 15 mm and a height between 1 and 5 mm. In another particular embodiment, said cylinder has a minimum perimetric area of 0.5 mm free of macropores. In other particular embodiments, the cylinder has:
   a diameter of 10 mm, a height of 5 mm, and 64 cylindrical macropores with a diameter of 500 μm±60 μm, uniformly separated from one another by 500 μm±60 μm which longitudinally traverse the matrix.
   a diameter of 10 mm, a height of 3 mm, and 64 cylindrical macropores with a diameter of 500 μm±60 μm, uniformly separated from another by 500 μm±60 μm which longitudinally traverse the matrix.
   a diameter of 8 mm, a height of 5 mm, and 39 cylindrical macropores with a diameter of 500 μm±60 μm, separated from one another by 500 μm±60 μm which longitudinally traverse the matrix.
   a diameter of 8 mm, a height of 3 mm, and 39 macropores with a diameter of 500 μm±60 μm, separated from one another by 500 μm±60 μm which longitudinally traverse the matrix.
   a diameter of 7 mm, a height of 5 mm, and 28 macropores with a diameter of 500 μm±60 μm, separated from one another by 500 μm±60 μm which longitudinally traverse the matrix.
   a diameter of 7 mm, a height of 3 mm, and 28 macropores with a diameter of 500 μm±60 μm, separated from one another by 500 μm±60 μm which longitudinally traverse the matrix.
   a diameter of 5 mm, a height of 3 mm, and 12 macropores with a diameter of 500 μm±60 μm, separated from one another by 500 μm±60 μm which longitudinally traverse the matrix.
respecting in all of them a perimetric area of 0.5 mm from the edge of said cylinder towards the center thereof, which is free of macropores.

Another object of the invention relates to the mold for preparing a three-dimensional matrix according to the previous objects of the invention, characterized by having a homogeneous distribution of punches of 350-650 μm in diameter uniformly separated from one another by between 0.4-0.6 mm. Said mold can be formed by silicone, metal, resistant plastic or any another material allowing its application, being able to adopt any type of required shape.

In a particular embodiment, the mold is in the form of a cylinder with a base diameter between 2 and 50 mm and a height between 1 and 50 mm. In another particular embodiment said cylinder has a base diameter between 2 and 15 mm and a height between 1 and 5 mm. In other particular embodiments, said cylinder has:
   a diameter of 10 mm, a height of 5 mm, and 64 cylindrical punches with a base diameter of 500 μm±60 μm, uniformly separated from one another by 0.5 mm±60 μm.
   a diameter of 10 mm, a height of 3 mm, and 64 cylindrical punches with a base diameter of 500 μm±60 μm, uniformly separated from one another by 0.5 mm±60 μm.
   a diameter of 8 mm, a height of 5 mm, and 39 cylindrical punches with a base diameter of 500 μm±60 μm, uniformly separated from one another by 0.5 mm±60 μm.
   a diameter of 8 mm, a height of 3 mm, and 39 cylindrical punches with a base diameter of 500 μm±60 μm, uniformly separated from one another by 0.5 mm±60 μm.
   a diameter of 7 mm, a height of 5 mm, and 28 cylindrical punches with a base diameter of 500 μm±60 μm, uniformly separated from one another by 0.5 mm±60 μm.
   a diameter of 7 mm, a height of 3 mm, and 28 cylindrical punches with a base diameter of 500 μm±60 μm, uniformly separated from one another by 0.5 mm±60 μm.
   a diameter of 5 mm, a height of 3 mm, and 12 cylindrical punches with a base diameter of 500 μm±60 μm, uniformly separated from one another by 0.5 mm±60 μm.
distributed in all of them respecting a perimetric area of 0.5 mm in width free of punches, taken from the edge towards the inside of the cylinder.

A following object of invention relates to the method of synthesis of the three-dimensional matrices of monetite with structured porosity characterized by comprising the steps of:
   1) mixing a solid phase formed by basic calcium phosphates, acidic calcium phosphates, a pore-inducing agent and a retarder, which is set by adding distilled water, giving rise to the liquid phase
   2) applying at least one mold in the cement during the setting to generate vertical cylindrical macropores of between 350 and 650 μm in diameter, uniformly separated from one another by 0.4-0.6 mm
   3) sterilizing the precursor material formed and heat-transforming it into monetite.

In a particular embodiment, in step 1 of the method, the molar ratio of basic phosphate/acidic phosphate is 1.6-1.8, the concentration of pore-inducing agent is 1-20% by weight, that of retarder is between 0.4-0.6% by weight and the (P/L) proportion is 3. In another particular embodiment, the molar ratio of basic phosphate/acidic phosphate is 1.785, the concentration of pore-inducing agent is 3-10% by weight and that of retarder is 0.54% by weight. In another particular embodiment, the acidic calcium phosphate is monocalcium phosphate, the basic calcium phosphate is beta-tricalcium phosphate, the pore-inducing agent is calcium carbonate and the retarder is sodium pyrophosphate. In another particular embodiment, the product of phase 1 is Brushite.

In another particular embodiment, in step 3 of the method, the heat sterilization is carried out by autoclaving. In another particular embodiment, said autoclaving is carried out at 120-130° C. and for 24-25 minutes.

In another particular embodiment, in step 2 of the method, the mold used is the mold described in the previous objects of the invention. In another particular embodiment, before using said molds, a silicone mold is used which is in the form of a cylinder with a base diameter between 2 and 50 mm, and a height between 1 and 50 mm. In another particular embodiment, said silicone mold has a base diameter between 2 and 15 mm and a height between 1 and 5 mm.

Another object of the invention is formed by the use of the mold described in the previous objects of the invention to obtain calcium phosphates adopting its shape. In a particular embodiment, said calcium phosphate consists of monetite.

Another object of the invention relates to the use of the three-dimensional matrices of monetite with structured porosity as a support for cell cultures.

Another object of the invention relates to the three-dimensional matrices of monetite with structured porosity characterized in that they additionally comprise cells. In a particular embodiment, said cells are mesenchymal cells, osteoblasts, osteoclasts, osteocytes, endothelial cells or combinations thereof.

Another object of the invention relates to the use of the three-dimensional matrices of monetite with structured porosity with or without cells to prepare a therapeutic agent for bone structure regeneration. In a particular embodiment, said bone structure regeneration is carried out to counteract osteoporosis.

DESCRIPTION OF THE DRAWINGS

The file of this patent contains at least one drawing executed in color. Copies of this patent with color drawing(s) will be provided by the Patent and Trademark Office upon request and payment of the necessary fee.

FIGS. 17a and b relate to the biomaterial without cells, FIGS. 17 c-h relate to the different cell concentrations used from $0.5 \times 10^6$ to $2 \times 10^6$ cells. FIGS. 18 a-h relate to the cell concentrations used $3 \times 10^6$ to $6 \times 10^6$ cells.

FIG. 19: Confocal microscopy images of the cells on (a) the surface of the monetite biomaterial with structured porosity of the invention and (b) inside the channels of the macropore of said biomaterial after several days in culture. The images of (b) show the nuclei of predifferentiated AMSCs inside the pores of the biomaterial (the reconstruction of the pore in its entirety is carried out by means of the montage of serial images). It is observed from these images how there is an increase of cells in the surface of the biomaterial as well as the walls of the macropores as the culture time increases.

FIG. 24 indicates the observations which must be made in reading each of the following FIGS. 25 to 31. Thus, as can be observed, FIG. 24 is divided into 4 quadrants: the top left quadrant (i) refers to the staining of the nuclei of the cells, the top right quadrant (ii) refers to the labeling of only the protein, the bottom left quadrant (iii) refers to the double staining of cell nuclei+protein and the bottom right quadrant (iv) relates to the triple staining in which the cell nuclei+protein+biomaterial are observed.

FIGS. 25-26: Confocal microscopy image of the immunolabeling of COL-1 of the predifferentiated AMSCs in the surface (topview, FIG. 25) and inside the channels (sideview, FIG. 26) of the biomaterial at different culture times.

FIG. 27-28: Confocal microscopy image of the immunolabeling of Osteocalcin in the predifferentiated AMSCs in the surface (topview, FIG. 27) and inside the channels (sideview, FIG. 28) of the biomaterial at different culture times.

FIGS. 29-30: Confocal microscopy image of the immunolabeling of osteopontin in the predifferentiated AMSCs in the surface (topview, FIG. 29) and inside the channels (sideview, FIG. 30) of the biomaterial at different culture times.

FIG. 31: Confocal microscopy image of the immunolabeling of type-1 collagen, osteocalcin and osteopontin in the predifferentiated AMSCs, growing on the surface of the biomaterial (topview, FIG. 31 a-c) and inside the channels (sideview, FIG. 31 d-f) for 4 days. These results indicate that the predifferentiated MSCs which are present in the biomaterial are capable of synthesizing and secreting proteins related to bone synthesis.

EXAMPLES

Figure 1:
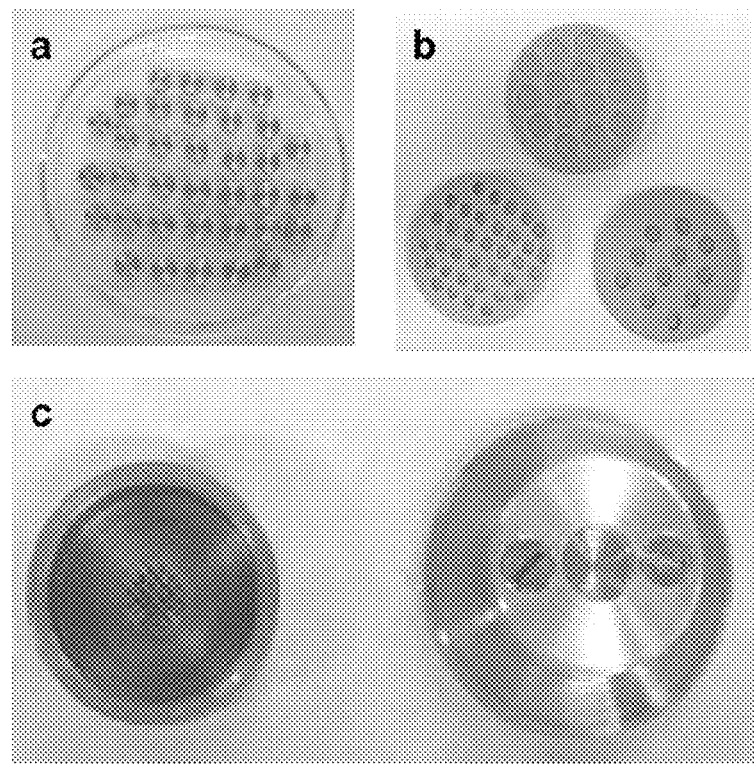
FIG. 1: a) Metal parts fixed in a glass plate of the same size as the Monetite cylinders which are to be synthesized b) Silicone molds obtained from the parts of FIG. 1a), with the cavities of the size of the parts which are to be manufactured, without taking into account for the moment the formation of the macropores c) Metallic mold with metallic punches which will give rise to a controlled and homogeneous macroporosity in the matrix of monetite.

The following examples serve to illustrate but do not limit the present invention.

Example 1

Method of Synthesis of the Matrices of the Invention

To synthesize the matrices of the invention, a solid phase was mixed with double-distilled water (liquid phase).

The solid phase comprises but is not limited to an acidic calcium phosphate, a basic calcium phosphate, a pore-inducing agent such as calcium carbonate and a setting retarder such as sodium pyrophosphate.

1.1 Preparation of the Solid Phase

The solid phase of the calcium cement is made up of a basic calcium phosphate and an acidic calcium phosphate. The basic calcium phosphate is beta-tricalcium phosphate (β-TCP) and the acidic calcium phosphate is monocalcium phosphate. The two components are mixed in a molar ratio of 1.785 in mortar by hand for 10 minutes. Calcium carbonate is added at concentrations between 1-20% (weight/weight) preferably between 3-10%. 0.54% (weight/weight) sodium pyrophosphate is used as a retarder of the setting reaction.

Specifically, to prepare beta-tricalcium phosphate (β-TCP) 34.42 g of DCPD and 10.01 g CC are mixed (in a molar ratio of 2:1) in a glass mortar and homogenized by hand for 15 minutes. The mixture is heated in an oven (Veckstar) at 900° C. for 14 hours. The synthesis of β-TCP occurs according to the reaction:

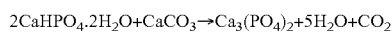

$2CaHPO_4.2H_2O+CaCO_3 \rightarrow Ca_3(PO_4)_2+5H_2O+CO_2$

The powder is then sieved and the powder having a particle size less than 322 μm is used.

1.2 Preparation of the Liquid Phase and Synthesis of Monetite Sponges

The liquid phase is formed by distilled or double-distilled water.

The solid phase formed by 0.8 g of monocalcium phosphate anhydrous, 1.4 g of beta-tricalcium phosphate, 12 mg of sodium pyrophosphate and 110 mg of carbonate is weighed and 0.77 ml of the liquid phase is mixed in a (P/L) powder-liquid ratio of 3 in a glass plate for 30 s.

1.3 Setting Process

The cement is set for 30 minutes in a water bath at 37° C. The setting reaction occurs according to the reaction:

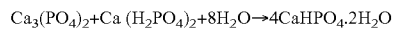

$Ca_3(PO_4)_2+Ca(H_2PO_4)_2+8H_2O \rightarrow 4CaHPO_4.2H_2O$

During the setting reaction the bicarbonate reacts with the hydrogen ions of the medium, decomposing into carbon dioxide, forming cavities and thus generating a spongy matrix of brushite.

1.4 Washing Process

The biomaterial is then washed several times in distilled water to eliminate remains of acids in the medium until reaching a pH close to 7, which is optimal for the cell growth which will be carried out in subsequent steps.

1.5 Process for Transforming Brushite into Monetite

Once the set material is obtained by means of the process described above, it is sterilized. The process for said sterilization comprises autoclaving the set material in a temperature range of 120-130° C. for 24-25 minutes. During this process the brushite is transformed into monetite.

Process for transforming brushite into monetite:

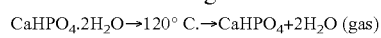

$CaHPO_4.2H_2O \rightarrow 120°C. \rightarrow CaHPO_4+2H_2O$ (gas)

1.6 Method of Synthesis of the Matrix of Amorphous Porous Monetite.

Figure 6:
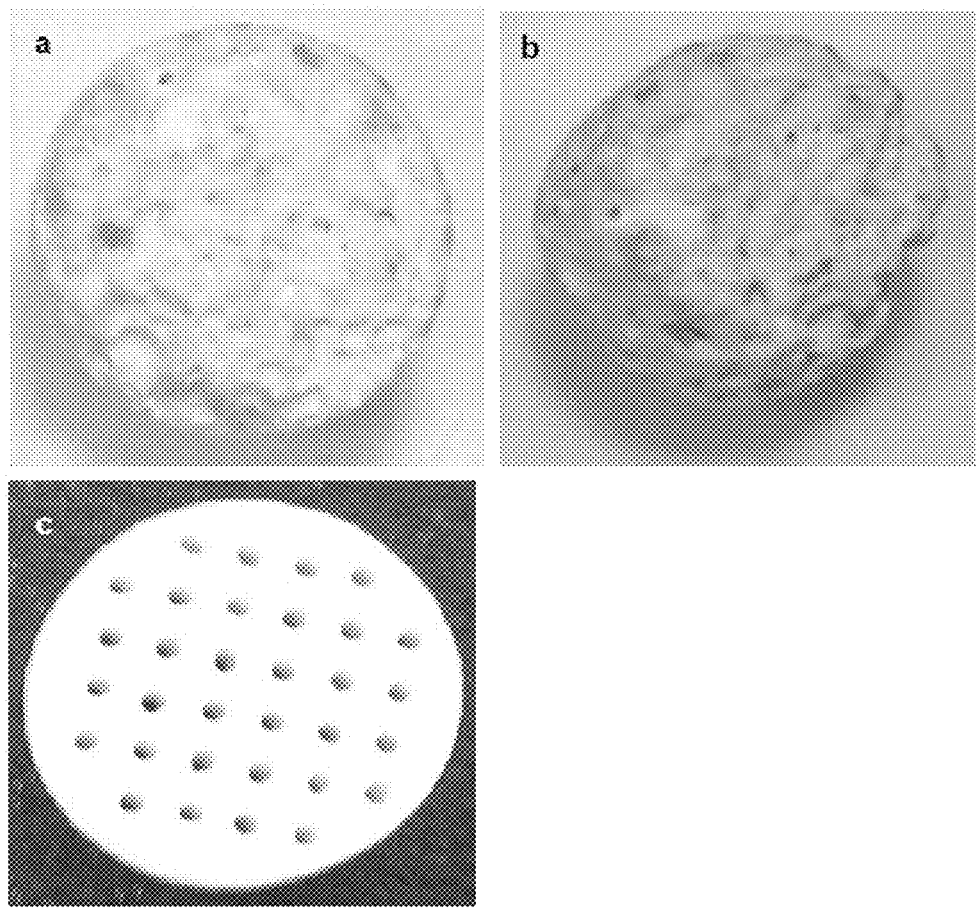
FIG. 6: Front (a) and side (b) images of the matrix of amorphous monetite, i.e., without the structured porosity. The porosity which is seen is inherent to the process for obtaining it, most of the porosity of the biomaterial is formed by micropores, in which cell colonization cannot be carried out. (c) Image of the design of the matrix of monetite of the invention with the pore sizes defined at about 500 μm, distributed in the structure of the biomaterial.

Once the compounds have been mixed as descried above (Example 1.1 to 1.2), the resulting cement, brushite, is placed on a surface with the shape of interest for the setting and the subsequent sterilization thereof, thus obtaining an amorphous matrix, with little presence of macropores and irregular distribution thereof, as can be observed in FIGS. 6a and b.

1.7 Method of Synthesis of the Matrix of Monetite with Structured Porosity

Figure 2:
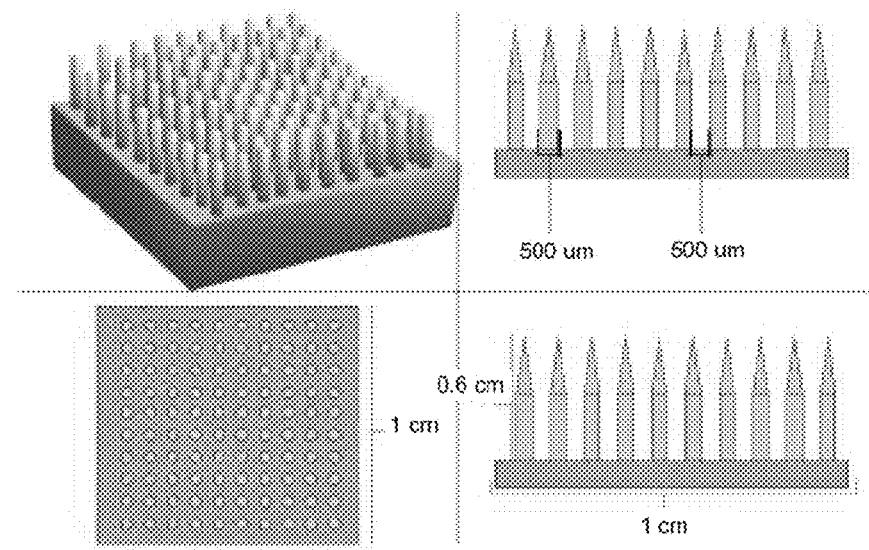
FIG. 2: Design of an example of a mold used to obtain the matrix of monetite, with a homogeneous distribution of vertical pores of 500±60 mm in diameter, regularly and reproducibly spaced.

After obtaining the cement by means of the process described in Examples 1.1 to 1.2, one minute after starting the setting, the silicone mold shown in FIG. 2 was applied to the cement for 30 seconds. Once the material has set, it is sterilized as described above (Example 1.5).

The use of different molds allows obtaining materials having cylindrical pores with a mean size of 500±60 μm and which allow connecting the micro- and macropores generated by the pore-inducing agent.

Figure 3:
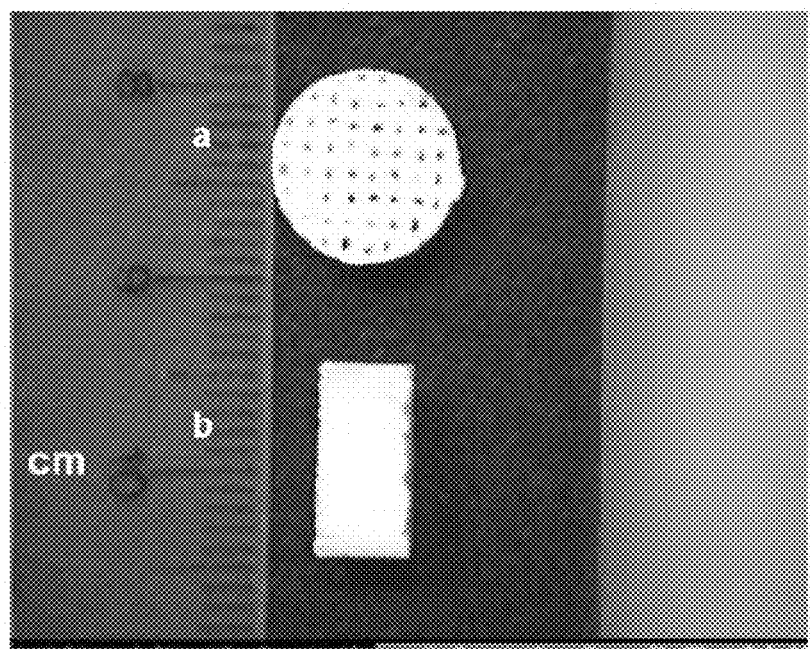
FIG. 3: Photograph of one of the forms of matrix of porous monetite seen in an elevational view (a) and in a profile view (b). This image shows the cylindrical pores with equal size, regularly distributed over the structure of the matrix and how these pores completely traverse the structure.

FIG. 3 shows an example of matrix of monetite with structured porosity produced by means of the process described in the invention. As a result of the generation of carbon dioxide during the setting reaction as well as the application of the mold described above, the resulting material shows a spongy appearance with a given distribution of pores. A sterile monetite biomaterial with structured porosity, which can be used without further treatments as a matrix for cell growth, is thus obtained.

Figure 4:
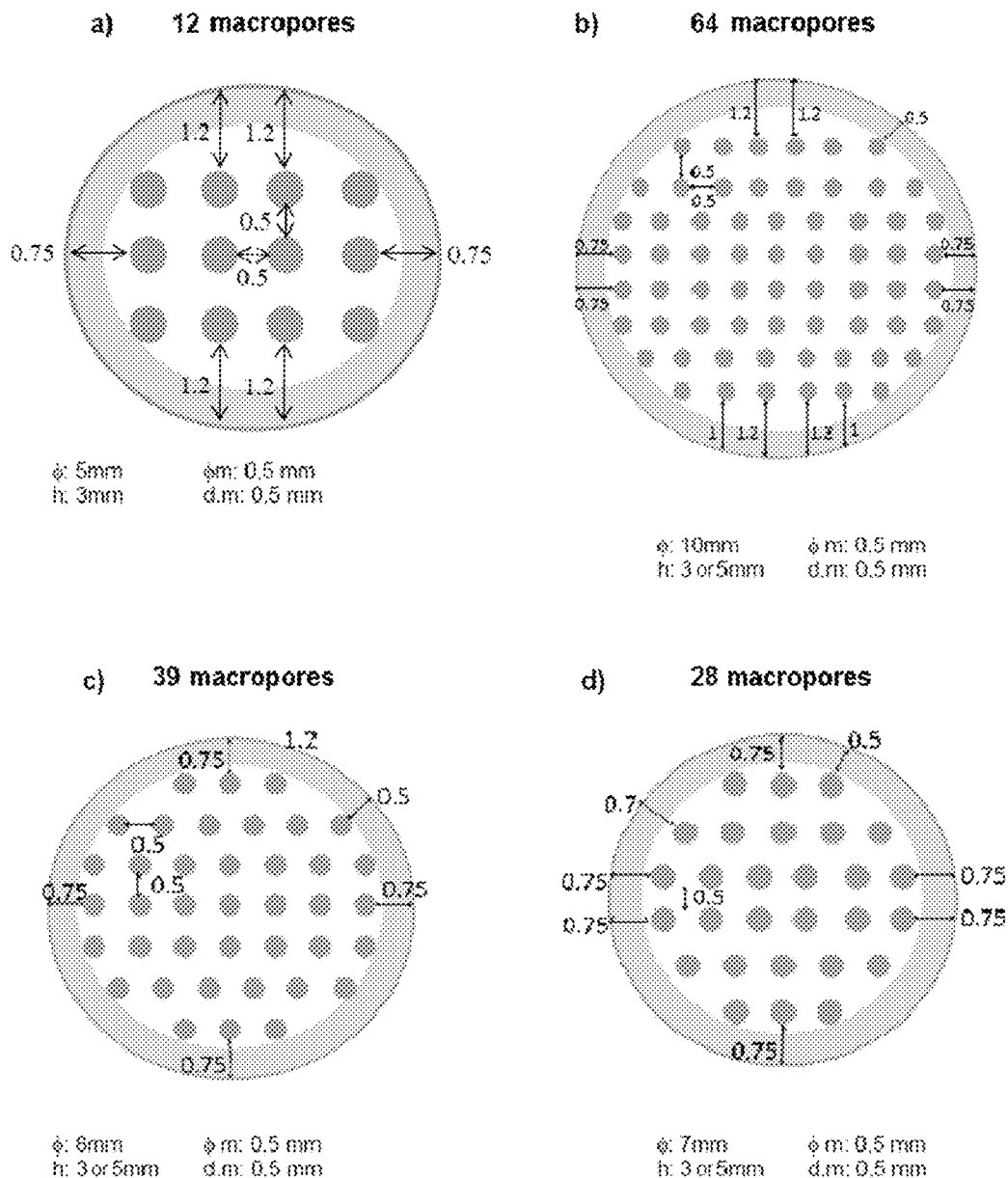
FIG. 4: Particular embodiments of the monomers/pellets of the invention and their dimensions a) pellet of 5 mm in diameter ($\phi$) and 3 mm in height (h) with a total of 12 macropores of 0.5 mm in diameter distanced ($\phi$.m) from one another by 0.5 mm (d.m) b) pellet of 10 mm in diameter ($\phi$) and 3 or 5 mm in height (h), with a total of 64 macropores of 0.5 mm in diameter ($\phi$.m) distanced from one another by 0.5 mm (d.m) c) pellet of 8 mm in diameter ($\phi$) and 3 or 5 mm in height (h) with a total of 39 macropores of 0.5 mm in diameter ($\phi$.m) distanced from one another by 0.5 mm (d.m) and d) pellet of 7 mm in diameter ($\phi$) and 3 or 5 mm in height (h) with a total of 28 macropores of 0.5 mm in diameter ($\phi$.m) distanced from one another by 0.5 mm (d.m). All of them respect the perimetric area of 0.5 mm in width free of macropores.
Figure 5:
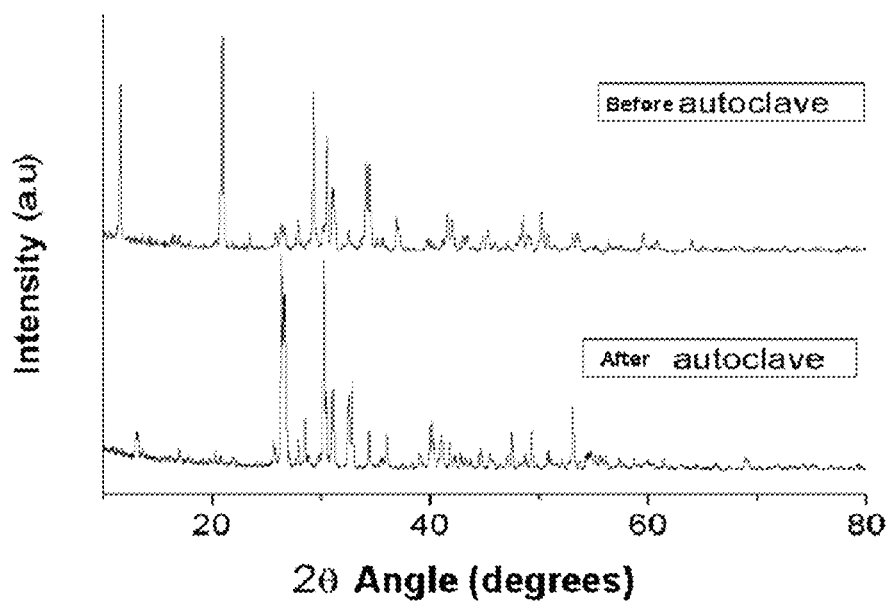
FIG. 5: X-ray diffraction of the precursor porous brushite (before the heat treatment) and porous monetite (after the heat treatment) obtained after the process for transforming and sterilizing the material. The 3 highest peaks appearing in the X-ray diffraction graph define in the case of the top graph (a) Brushite and in the bottom graph (b) are typical of monetite. The structural analysis of the samples (Rietveld analysis) after the autoclave sterilization shows that the material mainly consists of 95±5% monetite and the rest is β-tricalcium phosphate (also referred to as β-TCP). To establish the composition of the material the diffraction diagram of the biomaterial was compared with model diagrams of brushite (ICSD 016132) and of monetite (ICSD 38128).

FIG. 5 shows the diffraction diagram of the samples before and after the heat treatment in the autoclave. It can be observed in FIG. 4 that, in addition to sterilizing the material, the heat treatment causes the crystalline transformation of the structure from brushite to monetite.

Example 2

Specific Production of Specific Monetite Pellets with Structured Porosity

By way of example and for the purpose of obtaining cements with optimal characteristics, the powder component formed by 0.8 g of monocalcium phosphate anhydrous, 1.4 g of beta-tricalcium phosphate, 12 mg of sodium pyrophosphate and 110 mg of calcium carbonate was mixed for 30 seconds with 0.77 ml of water. One minute after starting the setting, the molds described below were applied to the cement for 30 seconds.

2.1 Use of a Single Mold in the Process for Obtaining Cylindrical Matrices of Monetite with Structured Porosity For the specific performance of this example, silicone molds with the following dimensions and number of punches were used:
 a) 1 cm in diameter, 5 mm or 3 mm in height and 64 punches
 b) 0.8 cm in diameter, 5 mm or 3 mm in height and 39 punches
 c) 0.7 cm in diameter, 5 mm or 3 mm in height and 28 punches
 d) 0.5 cm in diameter 3 mm in height and 12 punches In all the molds, the punches are cylindrical, with a diameter comprised between 500 µm±60 µm, separated from one another by 500 µm±60 µm, and distributed respecting a perimeter of 0.5 mm (taken from the edge towards the inside of the mode) free of punches. The structure of said punches is that of those depicted in FIG. 2.

During the setting reaction, as described in Example 1.7, the bicarbonate reacts with the hydrogen ions of the medium, decomposing into carbon dioxide, forming cavities and thus generating a spongy matrix of brushite.

The biomaterial is then washed several times in distilled water to eliminate remains of acids in the medium until reaching a pH close to 7, which is the optimal one for cell growth.

The material is subsequently sterilized. In the autoclave sterilization process at 1° C. for 24 minutes, brushite is transformed into monetite, thus obtaining a sterile monetite biomaterial which can be used without further treatments as a matrix for cell growth.

Thus, the resulting material consists of the specified spongy cylindrical pellets, formed by the biomatrix with structured porosity of the invention, with the dimensions indicated in each case, with macropores distributed homogeneously in said pellets.

The use of each of the indicated molds allowed obtaining the following matrices with homogeneously distributed cylindrical pores, with a mean pore size of 500 µm±60 µm, separated from one another by 0.5 mm±60 µm, which allow connecting the micro- and macropores generated by the pore-inducing agent:
 a) cylindrical pellets of 1 cm in diameter, 0.5 cm or 0.3 cm in height and with 64 macropores (FIG. 4b)
 b) cylindrical pellets of 0.8 cm in diameter, 0.5 cm or 0.3 cm in height and with 39 macropores (FIG. 4c)
 c) cylindrical pellets of 0.7 cm in diameter, 0.5 cm or 0.3 cm in height and with 28 macropores (FIG. 4d)
 d) cylindrical pellets of 0.5 cm in diameter, 0.3 cm in height and with 12 macropores (FIG. 4a)

As shown in FIG. 4, these monetite pellets of the invention obtained have a perimeter of 0.5 mm (taken from the edge of the pellet towards the inside thereof) free of macropores, allowing them to maintain the conditions of mechanical stability and strength necessary for being used in their applications.

2.2 Use of Two Molds in the Process for Obtaining Cylindrical Matrices of Monetite with Structured Porosity For the specific performance of this example, two types of mold, one made of silicone (FIG. 1b) and the other one made of metal (FIG. 1c), were used.

The silicone mold is used to obtain the Monetite cylinders of suitable size (without intervening in this phase in the formation of the macroporosity).

To synthesize the silicone mold, cylindrical parts with the same size as the Monetite parts which were to be obtained (FIG. 1a) were first fixed in a glass plate.

Liquid silicone was then added on the glass plate with the metallic parts, and its polymerization was awaited. Once polymerized, it was removed from the glass plate. The silicone molds obtained have cylindrical cavities of the size of the Monetite units which are to be manufactured (FIG. 1b). Said silicone molds with the cavities of the size of the parts which are to be manufactured do not have punches and, therefore, do not yet contemplate the formation of the macropores.

7 different silicone molds were obtained, having cylindrical cavities of the following dimensions:
 diameter of 10 mm and height of 5 mm or 3 mm,
 diameter of 8 mm and height of 5 mm or 3 mm,
 diameter of 7 mm and height of 3 or 5 mm,
 diameter of 5 mm and height of 3 mm.

In addition, metallic molds with the dimension of each Monetite part obtained with each of the indicated silicone molds were manufactured. Said metallic molds are made up of two parts, a first part having the punches which give rise to the reproducible macroporous component and a lid (FIG. 1c). Specifically, the dimensions of the manufactured metallic molds were the following:
 a) 1 cm in diameter, 0.5 cm or 0.3 cm in height and 64 punches
 b) 0.8 cm in diameter, 0.5 cm or 0.3 cm in height and 39 punches
 c) 0.7 cm in diameter, 0.5 cm or 0.3 cm in height and 28 punches
 d) 0.5 cm in diameter, 0.3 cm in height and 12 punches In all the molds, the punches are cylindrical, with a diameter comprised between 500 µm±60 µm, separated from one another by 500 µm±60 µm, and distributed respecting a perimeter of 0.5 mm (taken from the edge towards the inside of the mold) free of punches.

Once the molds have been manufactured, the monetite parts were created according to the following process:
 Firstly, the silicone molds were filled with the product which immediately resulted from mixing the solid phase and the liquid phase.
 Secondly, before the biomaterial ended its setting, the parts were removed from the silicone mold. The process is simple since the mold is like a very flexible rubber.
 Thirdly, the parts were introduced in the metallic mold with the punches and covered. Said mold is introduced in a water bath at 37° C. for 30 minutes until the end of the setting.
 Once completely solidified, they were removed from the metallic mold, obtaining cylindrical parts with the desired porosity.

The matrices formed were subjected to autoclaving between 120 and 130° C. for 24-25 minutes, their conversion into Monetite, completely sterilized and suitable for its use, occurring.

The parts obtained have the same porosity and dimensions as the parts obtained in Example 1a (FIG. 4).

Example 3

Comparative Studies Between the Matrices of Monetite with Structured Porosity and Amorphous Monetite 3.1 Microscopic Study A comparative assay of microscopic structure of the amorphous matrices and of the matrices with structured porosity of the invention was then carried out. To carry out said assay, scanning electron microscopy techniques by means of known processes for a person skilled in the art were used.

Microscopic Structure of the Matrix of Amorphous Porous Monetite

Figure 7:
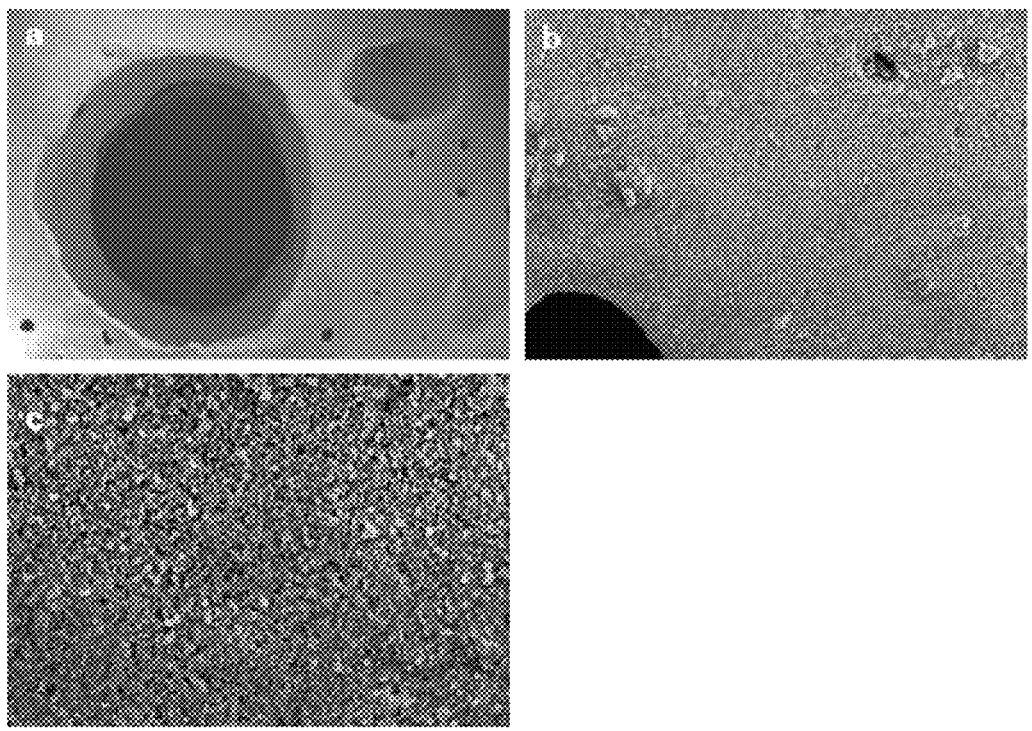
FIG. 7: Scanning electron microscopy images at different magnifications of the monetite biomaterial without controlled porosity. These images show a biomaterial which is fundamentally microporous (c) and with the minimum presence of some macropores (b) arranged randomly, like hollows, which in no case traverse the matrix (a, b).

The biomaterial arranged in the form of amorphous matrix (FIGS. 6 a, b) obtained an uncontrolled porosity. In other words, they show an irregular distribution of macropores, produced during the process for obtaining the cement, described in Examples 1.1 to 1-6. The macropores of the amorphous matrix are cavities in the biomaterial and do not connect the internal structure (FIG. 7).

In relation to the number and distribution of macropores, the scarcity thereof is observed. The presence of macropores is minimum and they are randomly arranged (FIG. 7).

Thus, these structures do not favor correct bone regeneration since they do not provide the conditions necessary for correct cell colonization and proliferation.

Microscopic Structure of the Matrix of Structured Porous Monetite

Figure 8:
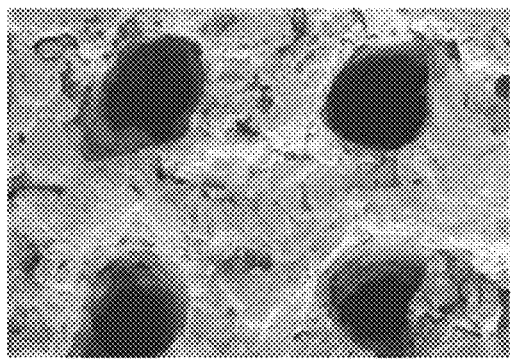
FIG. 8: Scanning electron microscopy image which shows the monetite biomaterial of the invention with 500 μm pores distributed over the matrix.

In contrast, FIGS. 6c and 8 show a matrix of monetite with structured macropores. The scanning microscopy image (FIG. 8) shows the homogeneous distribution of the macropores.

In contrast to the previous structure, the matrix of monetite with structured porosity will favor correct bone regeneration since it provides the conditions suitable for correct cell colonization and proliferation.

3.2 In Vivo Comparative Study

One of the most relevant aspects when designing a biomaterial for promoting bone regeneration is developing a structure having a porosity suitable for cell colonization and diffusion of gases and nutrients. Particularly, the macropores (of 100 to 500 µM) allow an optimal medium for the integral colonization of the cells supplied in the matrix, as well as the neovascularization and migration of osteoblasts and osteoclasts of the implant area and the homogeneous formation of new bone in the entire structure provided.

The biomaterial with structured porosity developed in the present invention has a characteristic macroporous structure which will allow a complete and homogeneous distribution of the osteogenic cells provided in the matrix and furthermore the entrance of cells of the recipient tissue, which will colonize and integrate the new structure, in order to start the resorption process thereof as well as to form new bone matrix which will be gradually deposited on the implant to give rise to new bone, with mechanical and physiological characteristics very similar to the original tissue.

To determine the advantage formed by the design developed in this work with respect to a non-structured porosity in macropores, a comparative study of the bone regeneration capacity between Monetite biomaterials without macropore structuring and with macroporosity structuring was performed.

To that end, sheep were used in which a critical defect in the tibia and a stabilization by osteosynthesis techniques were performed. In the defect created, the non-structured Monetite biomaterial was applied in 3 of them and the structured one was applied in the other 3, leaving in all of them the adjacent leg as a control (with formation of the critical defect and stabilization of the fracture but without filling of biomaterial). Before the implantation of the biomaterials, the latter were seeded with an identical number of mesenchymal stem cells from the adipose tissue obtained from the sheep.

To determine the formation of new bone, a continuous radiographic control and a histological study at 3 and 6 months after the implantation were performed. The results show a clear advantage of the biomaterial with macroporosity with respect to the one which does not have macroporosity. After 3 months from the implantation, a greater colonization of the osteoblasts and osteoclasts of the bone in the entire structure of the macroporous biomaterial, and the homogeneous formation of new bone can be observed. At 6 months, a complete integration of the macroporous material with the design of the invention is observed, with formation of a new vascularization, which will allow the generation of a stable bone, with diffusion of nutrients and oxygen in its entire integrity and without the formation of necrotic areas. However, when the biomaterial does not have a macropore structuring, the formation of new bone tissue restricted to the area peripheral to the implant is observed, leaving the rest of the matrix without cell colonization, either by the previously seeded cells or by those of the recipient tissue, and furthermore the formation of a new vascularization is not induced.

These results allow concluding that macroporous Monetite has evident advantages with respect to the formation of new bone, due to the colonization of the entire structure of the matrix by the cells of the implantation area, to give rise to a resorption, bone matrix formation and induction of a new vascularization, in a homogeneous manner.

Example 4

In Vitro Biocompatibility Studies

Before combining the monetite material with structured porosity of the invention with cells, it is necessary to demonstrate that said material is biocompatible.

The in vitro assays performed were related to cytotoxicity, genotoxicity (mutagenicity) and hemocompatibility, taking into account that the monetite biomaterial with structured porosity of the invention can be considered as an implantable product which will be in permanent contact with bone, the duration of the contact being greater than 30 days.

4.1 Cytotoxicity

Using cell culture techniques, these assays determine cell lysis (cell death), the inhibition of cell growth and other effects on cells caused by the healthcare products, the materials and/or the extracts thereof.

By means of this assay it is determined if the material under study, Monetite with structured porosity, is toxic for the cells, affects their proliferation and viability.

The material analyzed was the matrix of monetite with structured porosity obtained in Example 1, with dimensions of 1 cm in diameter, 5 mm in height and 64 macropores, using PVC as a Positive Control and high-density polyethylene as a Negative Control.

In relation to the conditions of extraction, since the thickness of the materials is >0.5 mm, 3 cm² of the material were contacted with 1 ml of the culture medium acting as an extracting agent.

The cell line used to test the cytotoxicity of the material was the L929 mouse fibroblast line cultured in DMEM culture medium with 10% fetal bovine serum.

The cytotoxicity and proliferation of monetite with structured porosity were determined by means of the MTT assay. This assay is based on the metabolic reduction of MTT by the mitochondrial enzyme succinate dehydrogenase in a colored compound (formazan) and determines the mitochondrial functional capacity of the cells which have been in contact with the monetite of the invention, according to the positive and negative controls established. The amount of live cells in the culture is thus proportional to the amount of formazan produced and therefore to the amount of absorbance registered by means of a spectrophotometer.

Figure 9:
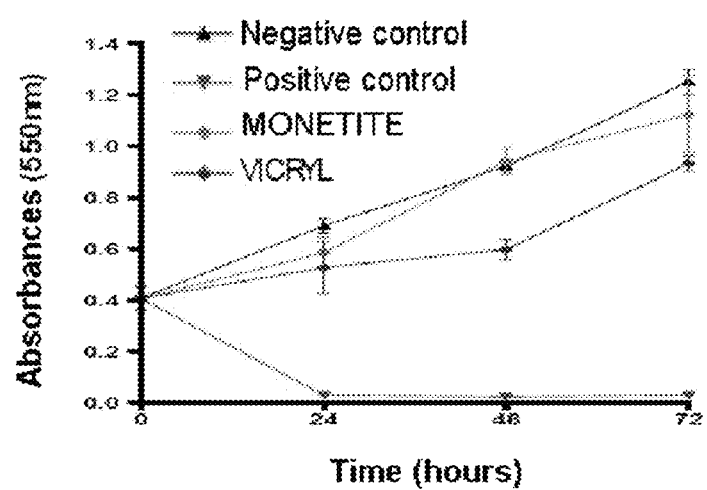
FIG. 9: Graph of the cytotoxicity study of the Monetite biomaterial of the invention in L929 cells. From the MTT assay it is observed that there are no significant differenced in the proliferation of L929 cells between those which have been in contact with monetite and those which have not, which allows concluding that the monetite with structured porosity of the invention is not cytotoxic.

A commercial cytotoxic standard biomaterial was used as a positive control, and high-density polyethylene and vicryl, also commercial, were used as negative controls. The graphic representation of the proliferation curves obtained for the L929 cells in each of the cases is observed in FIG. 9.

The results obtained do not show significant differences between the proliferation of the L929 cells in structured Monetite of the invention and in the negative control, demonstrating that the matrix of monetite with structured porosity of the invention is not a cytotoxic biomaterial.

4.2 Mutagenicity

In the genotoxicity assays, mammalian or non-mammalian cell cultures or other techniques are used to determine gene mutations, changes in the structure or in the number of chromosomes and other DNA or gene alterations caused by the toxicity of the healthcare products, the materials and/or the extracts thereof.

Figure 10:
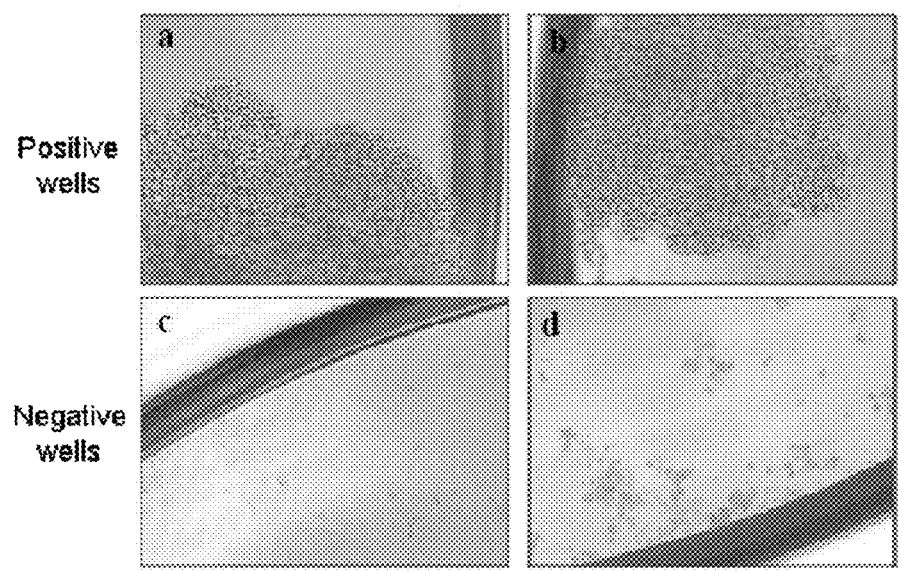
FIG. 10: Phase contrast inverted microscopy images obtained from the Mouse Lymphoma Assay. As a result of the assay, representative images of wells considered as (a) and (b) positive (mutant cells, colony growth) or (c) and (d) negative (non-mutant cells, absence of colonies) are shown.

The in vitro mutagenic potential of the Monetite with structured porosity of the invention was determined by means of the assay referred to as "Mouse Lymphoma Assay". Said assay is based on quantifying mutations in the thymidine kinase gene in L5178TK+/− mouse lymphoma cells, induced or non-induced after the treatment of these cells with the Monetite biomaterial with structured porosity. The cells deficient in the Thymidine Kinase (TK) gene due to the TK−/− mutation are resistant to the cytotoxic effects of trifluorothymidine (TFT). The cells capable of producing TK are sensitive to TFT, which inhibits the metabolism and stops cell division. Therefore, mutant cells are capable of proliferating in the presence of TFT, whereas normal cells containing at least one allele of the TK gene are not. The assay was performed in 96-well plates and the final result was obtained after visually counting the positive wells (FIGS. 10 *a* and *b*, in which the growth of a colony of cells is observed) and the negative wells (FIGS. 10 *c* and *d*, in which no growth is observed). Once the positive and negative wells of each 96-well plate have been counted, a series of formulas established for the assay are applied and the results are expressed in terms of mutation frequencies.

To carry out the assay, the cells were exposed to the product to be tested in the presence and absence of a suitable metabolic activation system, given that it can occasionally occur that a product to be tested is not mutagenic, but that the metabolites generated in vivo from that product are mutagenic.

The system most commonly used to simulate the hepatic metabolism in vitro is a post-mitochondrial fraction referred to as S9 to which cofactors are added and which is obtained from rat livers treated with enzyme inducers such as Aroclor 1254. Thus, before the cell treatment, the product to be tested is treated for 2 h with the mixtures referred to as S9, and after that time the cells are treated with the supernatant obtained from this mixture after centrifuging it.

The following products were used for the treatment of the cells:
  As positive controls:
    Methyl methanesulfonate (MMS) in the absence of metabolic activation.
    3-methylcholanthrene (3-MCA) in the presence of metabolic activation.
  As negative controls:
    Medium of L5178YTK+/− cells incubated for 24 h.
    Medium of L5178YTK+/− cells in the presence of metabolic activation incubated for 24 h.
  As product to be tested:
    Medium of L5178YTK+/− cells incubated for 24 h with the Monetite biomaterial.
    Medium of L5178YTK+/− cells incubated for 24 h with the Monetite biomaterial in the presence of metabolic activation.

Figure 11:
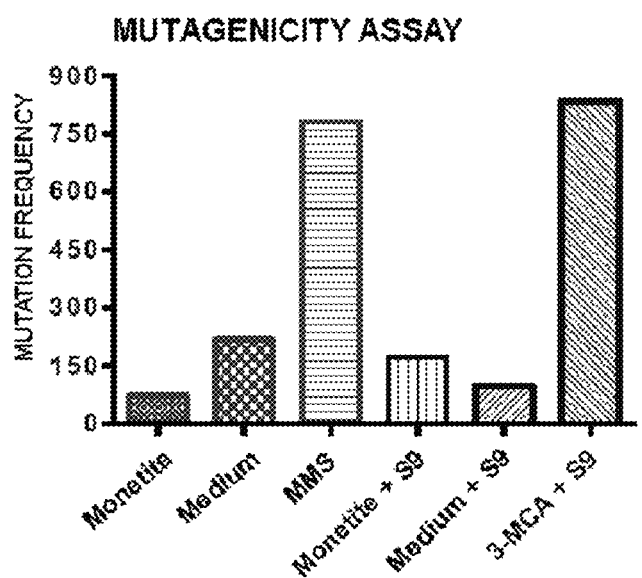
FIG. 11: Histogram of mutation frequencies of the Monetite with structured porosity of the invention in the presence (Monetite+S9) and absence (Monetite) of metabolic activation. Said frequencies compared to the negative and positive controls used in the presence and absence of metabolic activation allow concluding that the monetite with structured porosity of the invention is not a mutagenic biomaterial.

The results obtained (shown in FIG. 11) show that both in the presence and in the absence of metabolic activation it is observed that the negative controls used in the experiment induce a low mutation frequency similar to that of the cells which have been cultivated in the presence of the Monetite with structured porosity. The existence of mutated cells cultured with their culture medium is due to the high spontaneous mutation rate of these cells, thus, this mutation frequency is established as background. In relation to the positive controls, the mutation frequency induced in the L5178YTK+/− cells is clearly higher (about 7 times higher in both cases) than that induced by Monetite or the culture medium. These results demonstrate that Monetite is not a mutagenic biomaterial.

4.3 Hemocompatibility

These assays evaluate the effects caused on blood or its components by healthcare products or materials which come into contact with blood, using a suitable model or system. The hemolysis assays determine the degree of lysis of the red blood cells and the release of hemoglobin caused by the healthcare products, the materials and/or the extracts thereof in vitro.

The hemocompatibility of the monetite with structured porosity of the invention was determined by means of a colorimetric assay for determining total blood hemoglobin and hemoglobin released into the plasma when the blood is exposed to monetite. Given that the biomaterial is in solid phase, culture media of cells (osteoblasts and AMSCs) which were in contact for 24 hours with monetite were tested. The results show that the coefficient of variation of the calibration, sample and quality control lines (% CV) is 20% in all the cases (except in the case of calibrator 6) and ⅔ of the values of the quality control line have a percentage of difference with respect to the theoretical one (% PVDF)≤20%, therefore the results of the assay are within the established acceptance criteria.

The percentages of hemolysis of the compounds used were the following, considering the value of concentration of hemoglobin of 10.19 mg/ml of the blood used as 100% hemolysis:

| Compound | Percentage of Hemolysis |
|---|---|
| Positive control: 1% Triton X-100 | 94 |
| Negative control: 40% Polyethylene glycol | 1.27 |
| Medium of bone | 0 |
| Medium AMSCs | 0 |
| Medium of bone + Structured monetite | 0 |
| Medium of AMSCs + Structured monetite | 0 |

Figure 12:
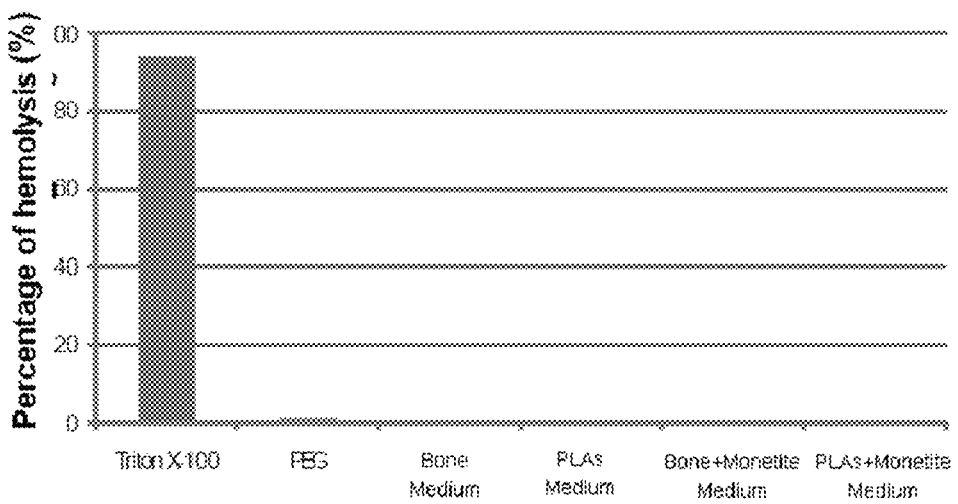
FIG. 12: Determination of the hemocompatibility of the monetite biomaterial of the invention. The culture media of osteoblasts and AMSCs which were in contact for 24 h with the monetite of the invention were used to determine the percentage of hemolysis compared to positive and negative controls. It can be concluded from the graph that the Monetite of the invention is a hemocompatible biomaterial.

These results, shown in FIG. 12, allow concluding that the Monetite with structured porosity of the invention is a hemocompatible biomaterial.

Example 5

Comparative Bioactivity Study Between the Matrix of Amorphous Porous Monetite and the Matrix of Monetite with Structured Porosity The bioactivity of a material will depend both on its physicochemical composition and on its structure.

Thus, in the present example a study is carried out to determine the effect of using the indicated amorphous matrix or matrix with structured porosity on the proliferative capacity of mesenchymal stem cells, one of the cell strains involved in the bone regeneration process together with the osteoblasts of the recipient tissue.

Once the porous biomatrix has been obtained, as described above, it was washed with culture medium with a pH of 7.4 for one or two hours to hydrate and neutralize the pH (changing the culture medium 2 or 3 times). Adult adipose tissue-derived mesenchymal stem cells (ATMCs) were directly seeded on the material, at a concentration of $0.5 \cdot 10^6$-$6 \cdot 10^6$ cells per cm². Two hours after the seeding, culture medium was added until covering the entire material, renewing it every two or three days.

The cells were cultured in the biomaterial for 7 days, after which the biomatrix to the surface of which the cells had adhered was analyzed by scanning electron microscopy (SEM), in order to observe the adhesion and colonization capacity of said cells on the porous monetite biomaterial.

Figure 13:
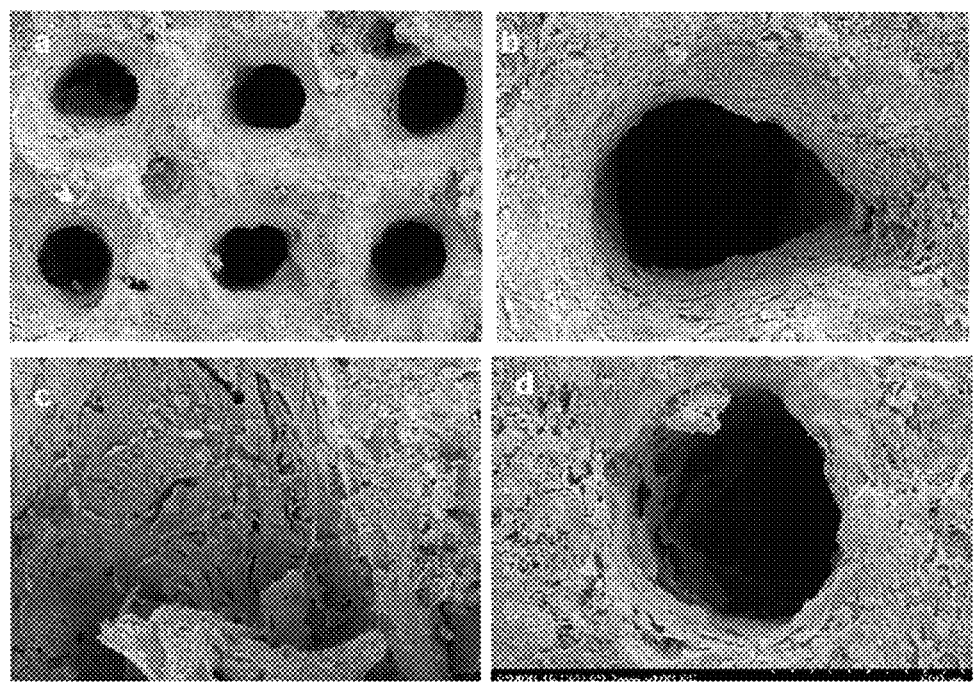
FIG. 13: Scanning electron microscopy images at different magnifications of a matrix of monetite with structured macroporosity according to the invention. The macropores allow the mesenchymal stem cells to colonize the surface of the biomaterial (a) and be introduced through said macropores (b, d). The longitudinal section of a macropore is observed in (c). (c) The cells interact with one another emitting cytoplasmic extensions, as occurs in a tissue at physiological level.

The images obtained by SEM (see FIGS. 13a and b), demonstrate that the mesenchymal stem cells are capable of adhering perfectly to the biomaterial, adopting a suitable morphology and that they furthermore establish intercellular contacts, as occurs in a tissue at physiological level (FIGS. 13c and d). As can be observed in FIGS. 13c and d the cells expand perfectly with the biomaterial, interacting maximally therewith and emitting cytoplasmic extensions (filopodia), which increase the surface of contact and increase the level of intercellular contact.

The biomaterial with structured porosity provides a larger surface to which the cells can adhere, in which they can proliferate and start performing their functions in the bone regeneration process. In other words, they can start creating new bone matrix which will substitute the biomaterial and express signaling molecules which will enhance and direct bone remodeling and neovascularization.

Figure 14:
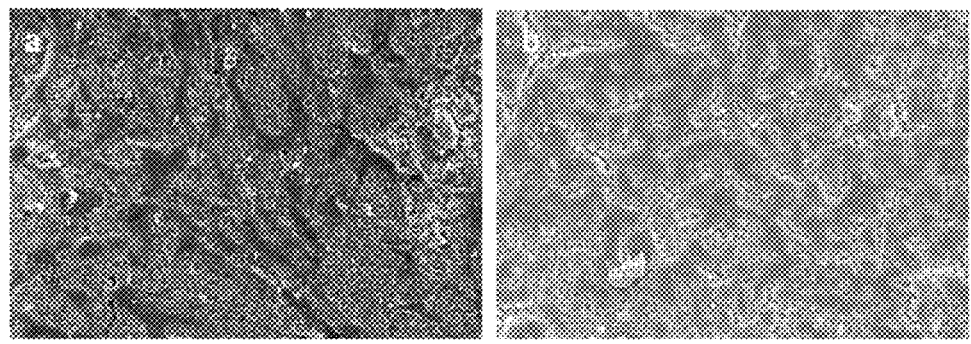
FIG. 14: Scanning electron microscopy images of the mesenchymal stem cells arranged in the monetite biomaterial with uncontrolled porosity. It can be seen that the cells are arranged in the surface of the matrix, without the possibility of colonizing its interior, since they have a significantly larger size than the microporosity characterizing the biomaterial.

In contrast, the use of the amorphous matrix as a support for cell growth shows that the random distribution of pores is not suitable for an efficient cell colonization to take place (FIGS. 14a and b), such cells being for the most part relegated to the surface of the matrix since they have a significantly larger size than the microporosity characterizing the biomaterial.

Figure 15:
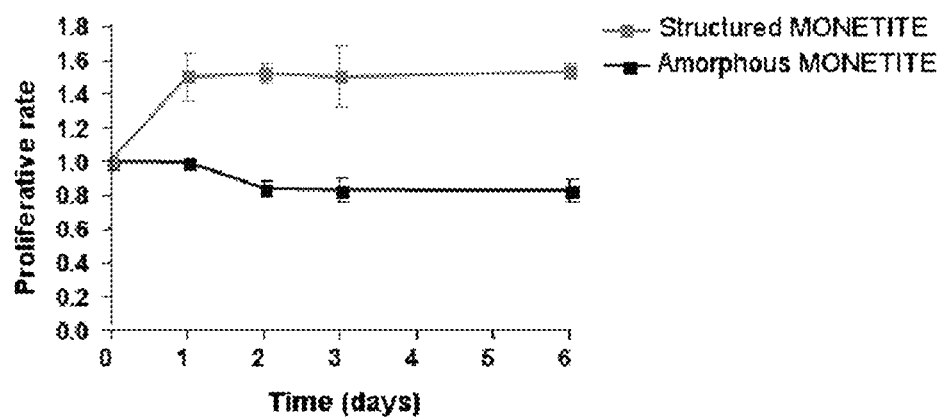
FIG. 15: Proliferation of the mesenchymal stem cells arranged on the monetite material with uncontrolled porosity (gray) compared to those arranged on the monetite biomaterial with structured porosity of the invention (black).
Figure 16:
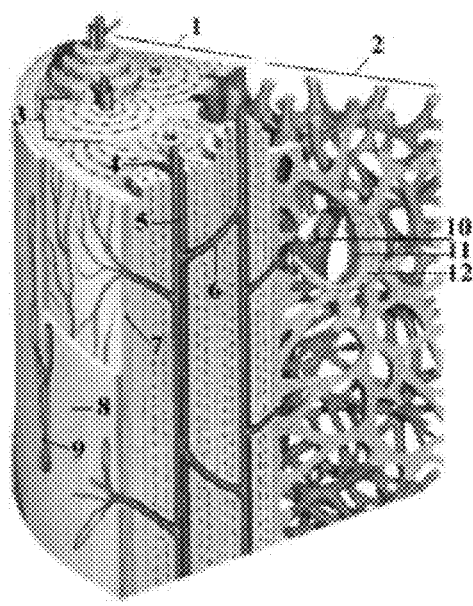
FIG. 16: Morphological diagram of bone tissue: 1. Cortical bone. 2. Trabecular bone. 3. Haversian system. 4. Blood vessel. 5 Haversian canal. 6 Volkmann's canal. 7 Periosteum. 8. Bone lining. 9. Periosteum vessels. 10 Osteoclasts. 11. Osteoblast. 12. Osteocytes.

The results, as shown in FIG. 15, demonstrate that a larger number of cells are quantified in the matrix of monetite with structured porosity. At 24 of culture, the cells in the matrix of monetite with structured porosity proliferate 1.5 times more with respect to those which are in the matrix of amorphous monetite, the proliferation being 1.8 times greater at 48 hours of culture.

In the matrix of the amorphous monetite, the cells over time give values of proliferation lower than the number of cells arranged at time 0 hours. These cells do not have room for being distributed and are compacted in the macropores without surface continuity, inhibiting the proliferation thereof and being located only in the surface of the material without the possibility of colonizing its interior, they could only be introduced in the small number of macropores which are randomly arranged. These macropores are in the form of hollows which in no case penetrate through the entire structure, which would hinder their interaction with the surrounding tissue in vivo and the arrival of nutrients and oxygen to all the cells. These cells can only be distributed over the surface of the biomaterial. These cells are compacted by lack of space, inhibiting the proliferation thereof and most of them being located only in the surface of the material.

However, the cells arranged in the matrix of monetite with structured porosity are distributed over all the pores, inside them and over the surface of the material, giving greater values of growth than time 0 hours. These cells are not compacted since they have a larger surface of contact with the material and therefore they do not inhibit the growth thereof.

Example 6

Determination of the Number of Cells to be Implanted Per Surface of Matrix

There are no studies which allow standardizing or knowing the optimal number of cells in this type of biomaterials, therefore the different investigators carry out their adaptations specifically in order to achieve the maximum clinical result.

In order for bone regeneration to be successful, the implant has to be integrated in the bone structure of the organism. To that end, the cells of the patient, (endothelial cells, osteoblasts, osteoclasts, macrophages, etc) have to interact with the product and colonize it, together with the supplied cells. In addition, an amount of cells in the product sufficient for the creation of a potent trophic effect, which activates the area and triggers the regenerative process, is necessary.

In order for the coexistence of cells of the patient and those of the product, a potent trophic effect of the product and a homogeneous cell distribution and diffusion of nutrients, gases and waste products of the metabolism to occur, the biomaterial must supply a large number of cells, but without said cells obturating the porous structure of the biomaterial.

Furthermore, the cell supply must be considerable since as the biomaterial is gradually degraded, it must be replaced by matrix synthesized by the cells themselves.

In conclusion, the suitable amount of cells is that which occupies virtually the entire surface of the biomaterial but which does not obturate the porous structure, for the following reasons:

Achieving the sufficient trophic effect to activate the bone regeneration process.

Synthesizing sufficient extracellular matrix to replace the biomaterial.

Allowing the arrival and settlement of cells of the patient involved in bone regeneration, including the endothelial cells in charge of neovascularization.

To determine the number of cells to be implanted per surface of biomaterial, increasing concentrations of cells were seeded in the biomaterial and the degree of colonization of the structure was observed under SEM. This study also allows determining if the form of seeding used is suitable for the distribution of the cells to be homogeneous.

The process used consisted of seeding monetite discs of 1 cm in diameter, 0.5 cm in height, and 64 macropores with a diameter of 500 µm, with increasing cell concentrations covering from half a million cells to 6 million per biomaterial ($0.5 \times 10^6$-$1 \times 10^6$-$2 \times 10^6$-$3 \times 10^6$-$4 \times 10^6$-$5 \times 10^6$-$6 \times 10^6$). The cells are maintained for 8 days in contact with the biomaterial, to allow the adaptation and settlement thereof. The results are analyzed by SEM.

Figure 17:
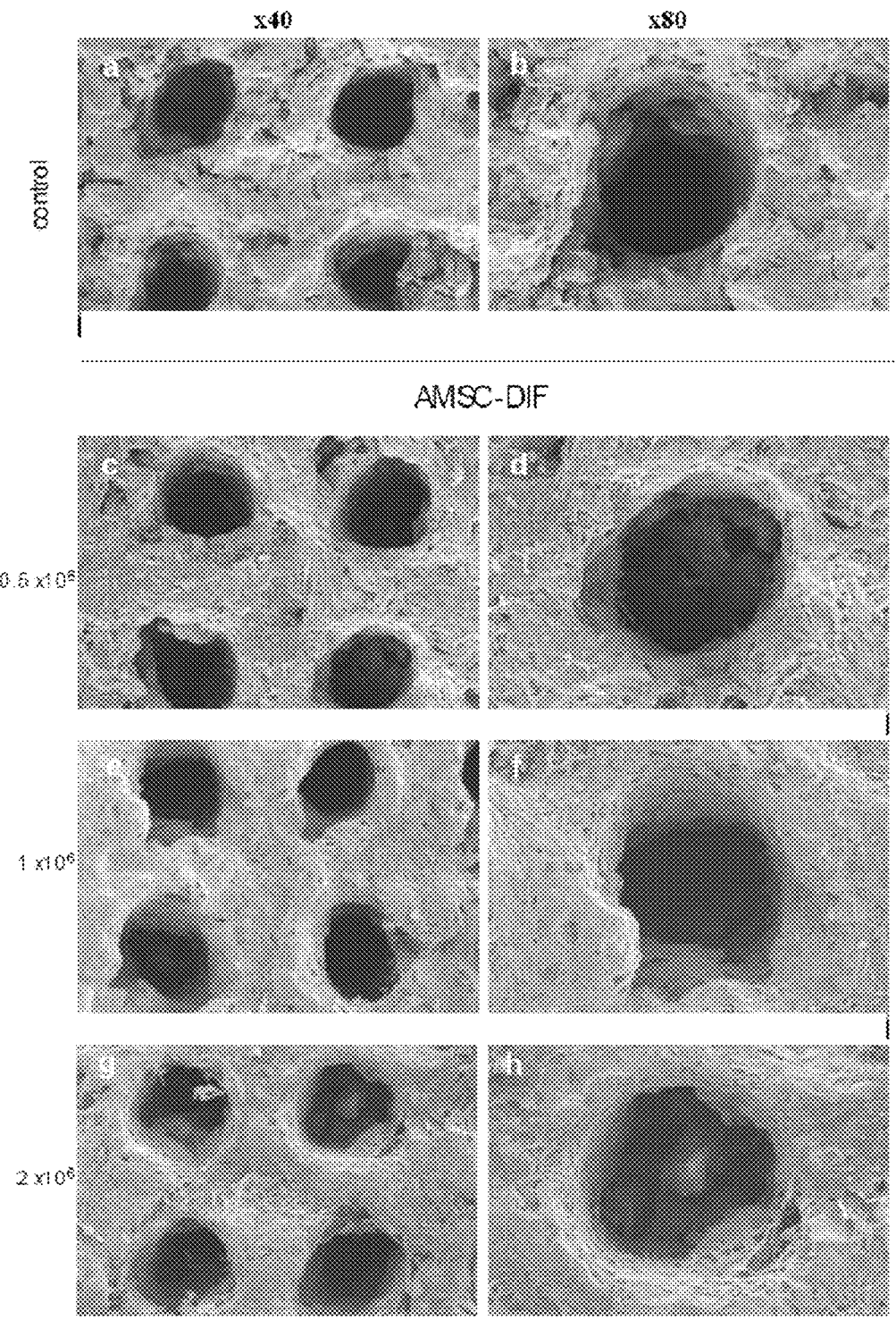
FIGS. 17 and 18: SEM images which show at a magnification of ×40 and at a magnification of ×80 how different concentrations of AMSCs predifferentiated into bone are arranged on one and the same surface of the biomaterial of the invention.
Figure 18:
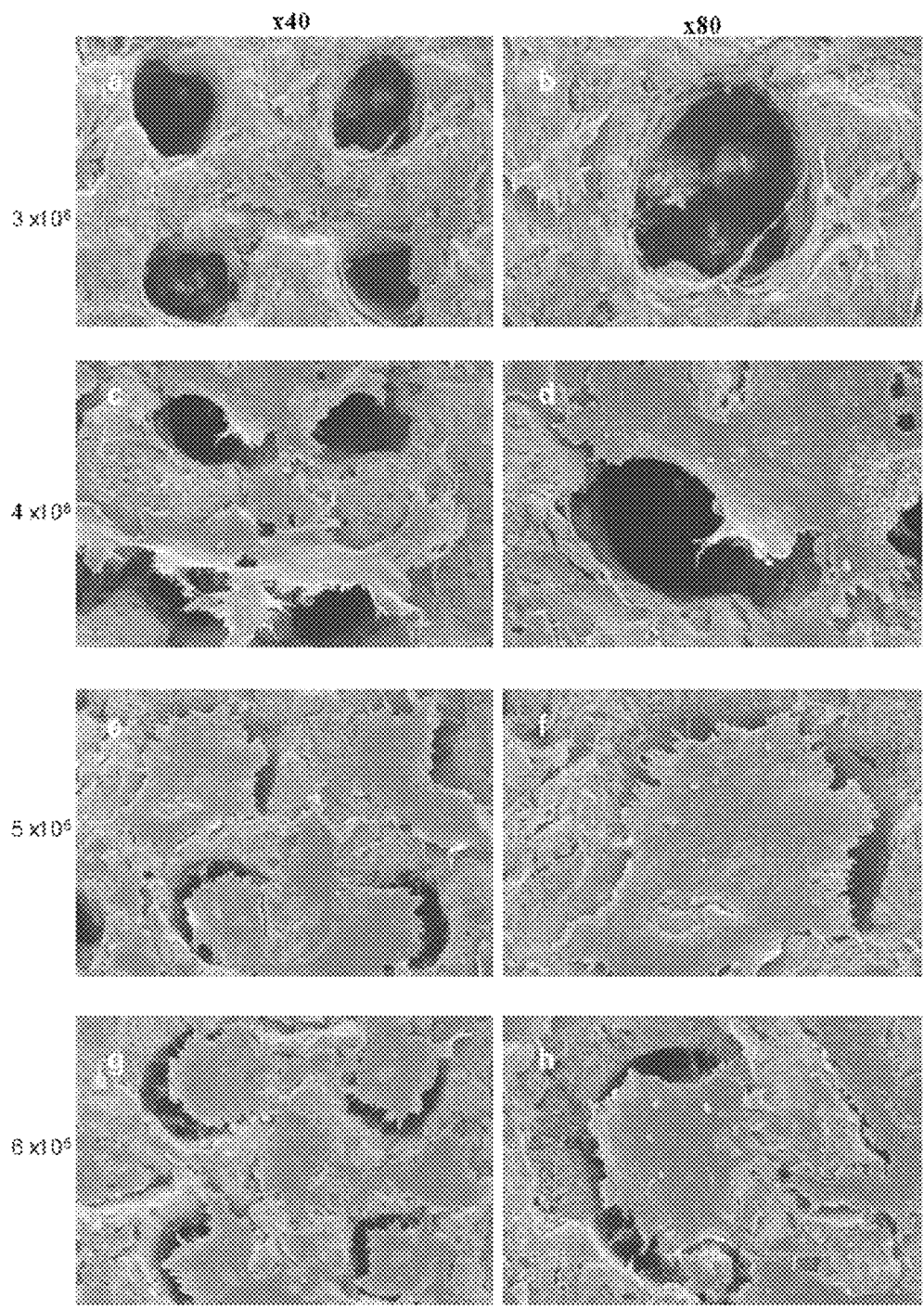

The images (FIGS. 17 and 18) indicate that as the cell concentration increases the degree of colonization of the monetite biomaterial with structured porosity of the invention increases, since the capacity of adhesion to the biomaterial is close to 100%. When the lowest dose is applied, the surface of the biomaterial does not show a complete invasion, but rather this phenomenon starts to be seen after the doses of $2 \times 10^6$ and $3 \times 10^6$ of cells. However, the 500 µm pores start to be obturated after seeding $4 \times 10^6$ cells and at the doses of $5 \times 10^6$ and $6 \times 10^6$ they are completely obturated. Furthermore, occupation of the inside of the pores of the biomaterial is already observed after the dose of $1 \times 10^6$ cells, said occupation increasing with the cell dose.

According to the results obtained, for the biomaterials used which have a total surface of contact of approximately 6 cm², a considerable amount of cells would be comprised between 2 and 3 million cells, which results in between 300,000 and 500,000 cells per cm².

Example 7

Analysis of the Evolution of the Cells in the Matrix. Analysis of the Cell State in the Matrix at Different Times Once the cell dose range suitable for the placement thereof in the biomaterial has been selected, the evolution of the cells in the biomaterial with structured porosity over time was then studied. To that end, an analysis of the cell behavior in vitro was carried out at different times.

7.1 Observation of the Predifferentiated Cells in the Matrix with Structured Porosity Over Time:

In order to be able to suitably observe the cells in the biomaterial with structured porosity, a direct observation by scanning electron microscopy (SEM) was performed and the cells were furthermore viewed with Hoechst nuclear staining by confocal microscopy. The viewing by SEM provides data about the affinity and capacity of interaction of the cells with the biomaterial, through the observation of the surface of contact. However, it is possible for the processing of the samples for SEM to eliminate cells from the biomaterial, which can be viewed by means of fluorescent techniques.

The following process was carried out:
Seeding 300,000 predifferentiated AMSCs per cm² of biomaterial.

Performing the processing for SEM or the Hoechst nuclear staining and viewing by confocal microscopy.

Analysis of the distribution and degree of interaction of the cells in the biomaterial after 1, 4, 7, 10 and 15 days of association.

The images of the results of observation by confocal microscopy show the Hoechst-stained cell nuclei in a very specific manner and with minimum background noise. Images of the cells in the surface of biomaterial (TOPVIEW) and inside the channels of the macropores (SIDEVIEW), after the controlled fracture of the biomaterial, were obtained.

The TOPVIEW image (FIG. 19a) shows that as the culture time goes by there is an increase in the number of cells in the surface of the biomaterial, which gradually cover the walls of the macropores and obturate the surface of all of them after 10 days of culture.

The SIDEVIEW image (FIG. 19b) is a montage of several serial images to be able to observe the cells in the entire length of the macropore. The cells colonize the interior of the channels from day 1 of association. As time goes by, a great cell coating and large aggregates at 10 and 15 days of culture are observed.

The images of the results of observation by SEM also show images of the surface of the biomaterial (TOPVIEW) and of the interior of the pore in its entirety (SIDEVIEW).

Figure 20:
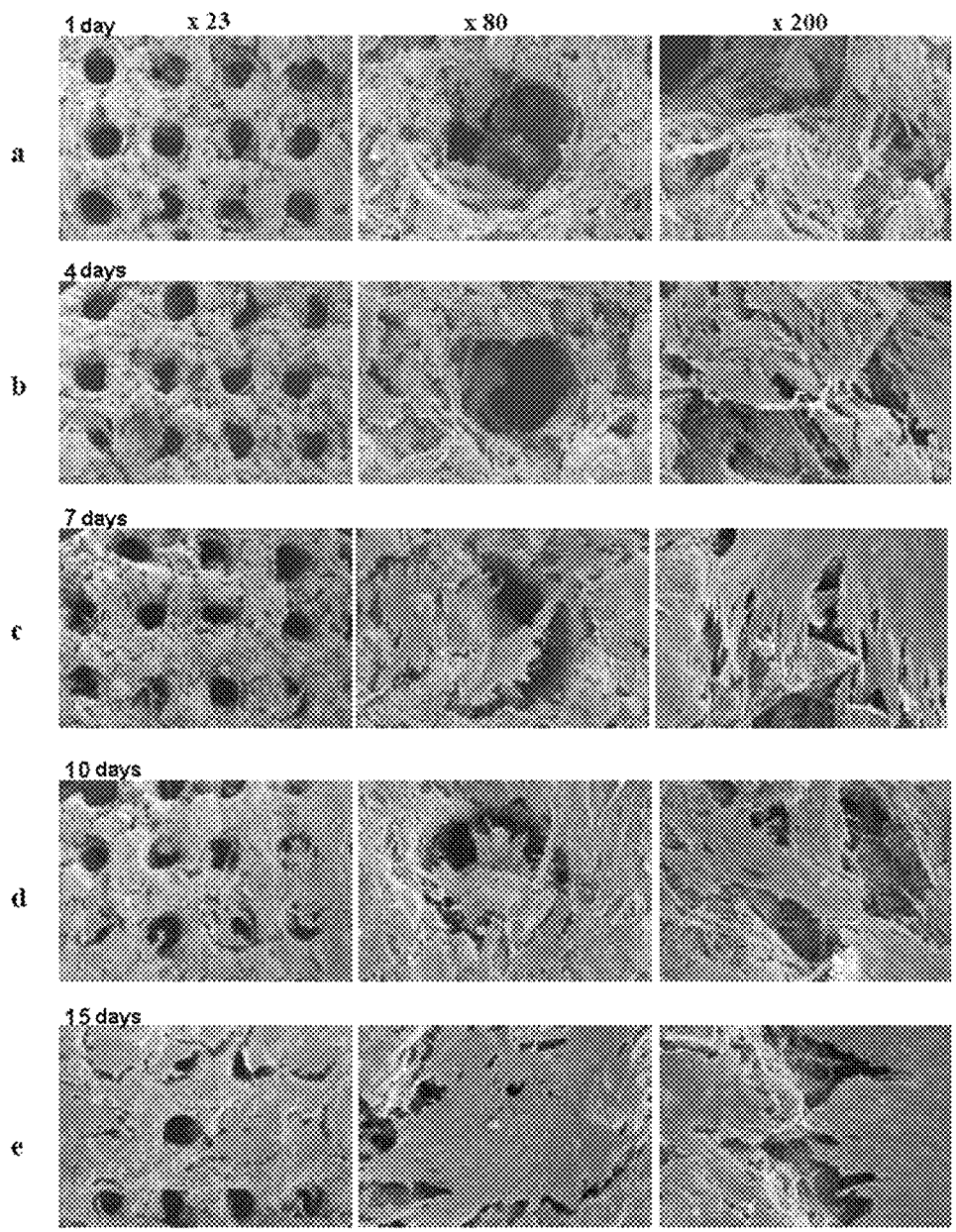
FIGS. 20 and 21: Zenithal SEM images at different magnifications of the predifferentiated AMSC cells in the biomaterial at different association times (1, 4, 7, 10 and 15 days in the surface of the biomaterial (FIGS. 20 a-e respectively)) and inside the channels of the macropores of the biomaterial (FIGS. 21 a-e respectively).

The TOPVIEW images (FIG. 20) show the increase of the degree of colonization as the culture time goes by. An obturation of the pores is observed after the $7^{th}$ day of culture, virtually all the pores being obturated at 15 days.

Figure 21:
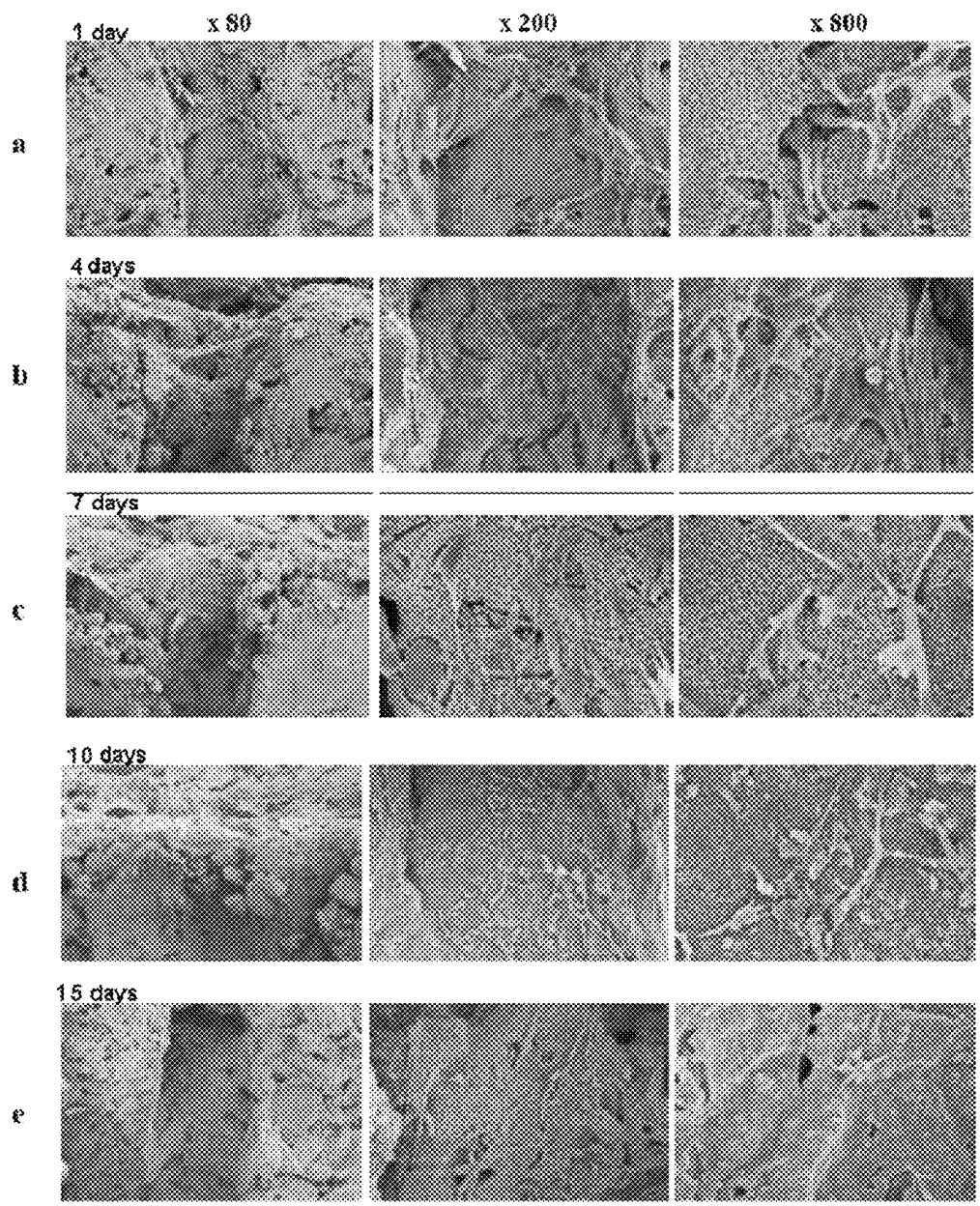

The SIDEVIEW images (FIG. 21) shows a smaller number of cells, even in the long times, due to losses occurring in the processing of the samples. However, a clear analysis of the nature of the interaction of the cells with the biomaterial using morphological criteria is offered. The cells show a large surface in contact with the biomaterial, observing a large number of cytoplasmic extensions, and they are furthermore even capable of being introduced in their internal structure.

Once the Hoescht and SEM images have been analyzed, it can be concluded that, at about 4 days, the AMSCs interact suitably and homogeneously with the monetite biomaterial with structured porosity of the invention, most of the surface thereof is invaded without the pores being obturated, which will allow the passage of nutrients and of host cells which will respond to the trophic call of the AMSCs.

7.2 Determination of the Osteoinductive Effect of the Monetite Material with Structured Porosity.

Analysis of the Gene Expression of Undifferentiated Adult Adipose Tissue-Derived Mesenchymal Cells (ATMCs), by Comparing the Structure of the Matrix of Monetite with Structured Porosity with Amorphous Monetite.

The Monetite biomaterial with structured porosity has a macroporous distribution favoring the homogeneous distribution of the cells over the entire matrix. Furthermore, this porous arrangement allows improving the arrival of nutrients, gases and the signaling molecules produced by the cells themselves. All this determines that the cells are in better conditions and can intercommunicate more effectively to express their osteogenic phenotype. For this reason, it is possible for the new structure of the biomaterial to enhance the osteoinductive effect of the nature of the matrix (a derivative of calcium phosphate, like bone) and induce the expression of genes related to osteogenic differentiation.

To determine this inductive effect of osteogenesis due to the new macroporous structure, analyses of the expression of genes related to bone differentiation are conducted by means of RT-PCR, comparing the structure of the matrix of amorphous Monetite with respect to the structured porous one.

To that end, the following experiment is carried out:

1.—Arrangement of adult mesenchymal stem cells derived from adipose tissue and human bone osteoblasts on the porous matrices of amorphous Monetite and of Monetite with structured porosity, at a concentration of 106 cells/cm$^3$.

2.—Maintenance in culture for 7 days on the biomaterials, to allow the structure of the biomaterial to act on cell behavior.

3.—Extraction of the RNA of the cells which are on the biomaterials and analysis of the expression of the following genes by means of RT-PCR: alkaline phosphatase, osteopontin, osteonectin and osteocalcin. These genes are directly related to the bone differentiation process and are activated as the mesenchymal stem cells and the osteoblasts carry out their differentiation process into bone.

The results indicate an induction of the expression of osteoconductive genes in the cells which are in the Monetite biomaterial with structured porosity with respect to the amorphous one.

In the mesenchymal stem cells there is an induction in the early differentiation genes osteopontin and osteonectin and to a lesser extent in the late differentiation genes alkaline phosphatase and osteocalcin, with respect to the cells arranged in the amorphous Monetite.

With respect to the osteoblasts, an induction of the expression of late differentiation genes such as alkaline phosphatase and osteocalcin is observed.

These results demonstrate that the structure of the biomaterial has a direct influence on cell behavior. The homogeneous macroporous distribution with pores capable of traversing the structure in its entirety, a greater porous interconnection occurring, allows greater intercellular communication and a better cell state due to the access to nutrients and gases. This situation allows expressing the cell phenotype more effectively and enhances the osteoconductive effect caused by the composition of the biomaterial.

This effect will be multiplied when the biomaterial is incorporated to the bone defect in vivo, wherein the osteogenic signals will be multiplied in the environment of the bone defect, so that a tissue repair can take place. These signals recruit bone osteoblasts and bone marrow mesenchymal stem cells, which may invade the biomaterial homogeneously and produce new bone matrix which will gradually substitute the biomaterial which is gradually resorbed, to cause a stable repair.

Study of the Maintenance of the Differentiation State of the Cells Arranged in the Monetite Biomaterial with Structured Porosity Over Time (Comparison of the Behavior of Predifferentiated and Undifferentiated ATMCs)

As indicated above, in addition to their arrangement and distribution, it is important to find out the functional state of the cells in the biomaterial with structured porosity over time, to determine the maintenance of the osteogenic differentiation state, i.e., if their orientation towards the formation of bone cells capable of synthesizing extracellular matrix which substitutes the biomaterial which is gradually degraded, in order to regenerate the bone defect, is maintained.

Figure 22:
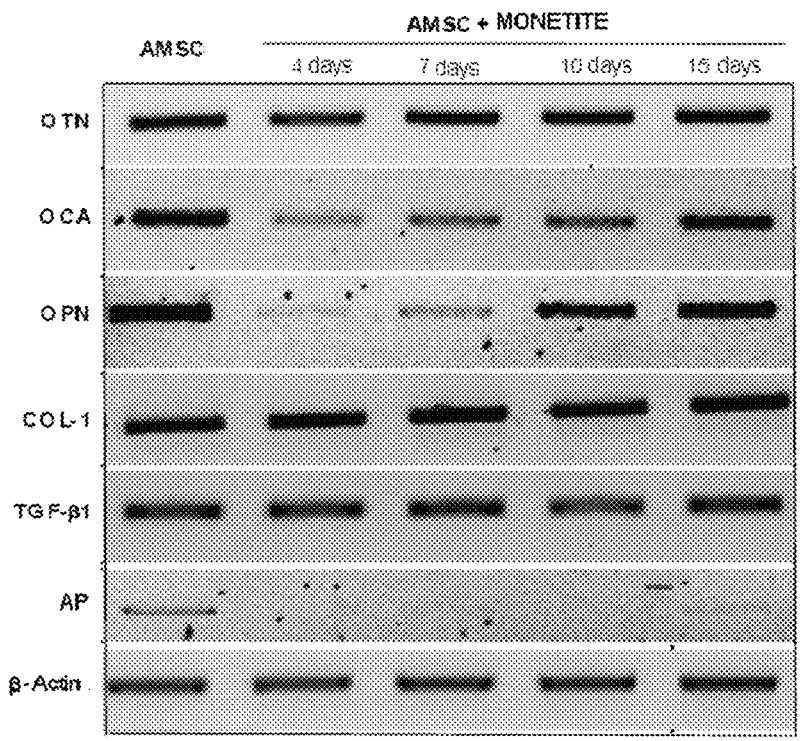
FIGS. 22 and 23: Analysis of the expression of the genes involved in the osteogenesis in AMSCs such as osteonectin (OTN), osteocalcin (OCA), osteopontin (OPN), type-1 collagen (COL-1), TGF-β1 and alkaline phosphatase (AP), by means of RT-PCR in undifferentiated (FIG. 22) and predifferentiated (FIG. 23) AMSC cells alone and associated with the biomaterial for 4, 7, 10 and 15 days. In view of the gels it can be concluded that both in the undifferentiated and the predifferentiated cells the expression of the genes involved in osteogenesis is not modified and that they therefore maintain their functional state aimed towards the formation of bone cells, capable of synthesizing extracellular matrix which substitutes the biomaterial which is gradually degenerated in order to regenerate the bone defect.

This study analyzed the maintenance of the expression of genes involved in osteogenesis in predifferentiated AMSCs arranged in the biomaterial. With this objective, the expression of the following genes involved in the osteogenesis process was analyzed by means of RT-PCR: osteopontin (OPN), osteocalcin (OCA), osteonectin (OTN), TGF-β1, alkaline phosphatase (AP) and type-I collagen (COL-1) (FIG. 22). The following process was carried out:

Arrangement of 300,000 undifferentiated and predifferentiated AMSC cells per cm$^2$ of the biomaterial.

Analysis of the expression of alkaline phosphatase, osteocalcin, osteopontin, type-1 collagen and TGF-β1, at the times of 1, 4, 7, 10 and 15 days in culture of association with the biomaterial.

In relation to the results with undifferentiated AMSCs, as can be observed in FIG. 22, the AMSC cells express all the genes studied, osteonectin, osteocalcin, osteopontin, type-1 collagen, TGF-β1 and the enzyme alkaline phosphatase.

This expression is not modified when they are cultured on the biomaterial with structured porosity at the analyzed times. Specifically, osteonectin, osteocalcin, type-1 collagen and TGF-β1 maintain their expression at 4, 7, 10 and 15 days of the culture on the biomaterial. The expression of osteopontin is reduced at 4 and 7 days, but recovers and is maintained at 10 and 15 days of culture in the biomaterial. However, the expression of the enzyme alkaline phosphatase is very slight in the AMSCs, is lost during the culture in the biomaterial and initiates its expression after 15 days of culture.

Type-1 collagen, osteopontin and osteonectin are expressed in an early manner in osteoprogenitor cells. Osteocalcin appears when mineralization starts. In this case, the AMSCs express both proteins involved in the start of osteoblast differentiation and in the final phase of said differentiation. Furthermore, they are capable of synthesizing collagen, which forms part of the organic component of the bone matrix. Once synthesized, these proteins can be absorbed and trapped in the new matrix which is formed.

Alkaline phosphatase is an enzyme which releases inorganic phosphorus from phosphoric esters, necessary for mineralization, i.e., it participates in bone mineralization and in the maturation of the osteoid matrix and therefore its expression is very late in the cell differentiation process.

TGF-β1 is a potent bone formation stimulator; it enhances osteoblast differentiation and bone matrix synthesis and inhibits the synthesis of matrix-degrading proteases. In fact, it is being used as a prognostic serological marker of the consolidation capacity in the pseudarthrosis progression process.

In relation to the results with predifferentiated AMSCs, when the cells are predifferentiated into bone for 8 days and arranged in culture on the Monetite with structured porosity of the invention (FIG. 23), there are no variations in the gene expression profile.

Figure 23:
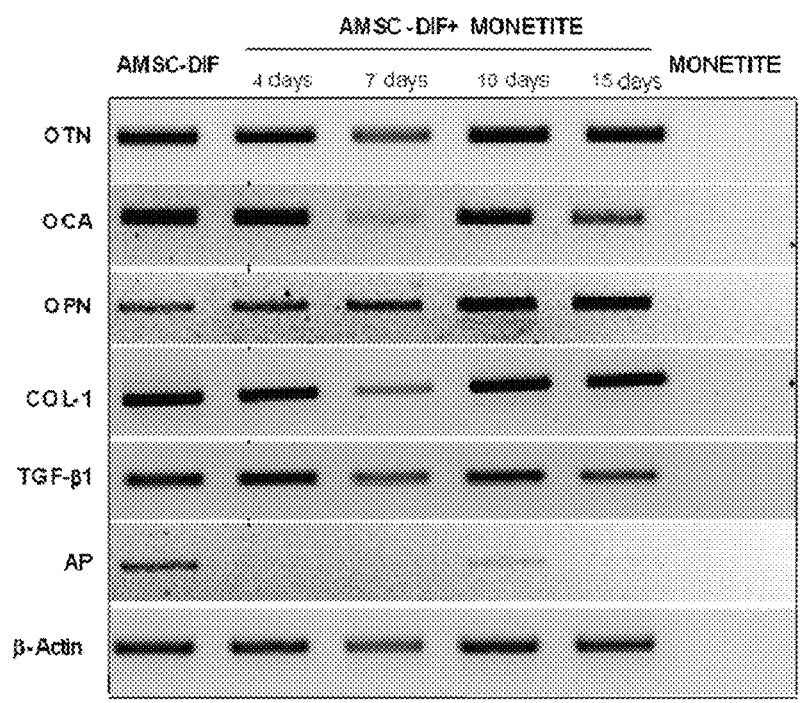
Figure 24:
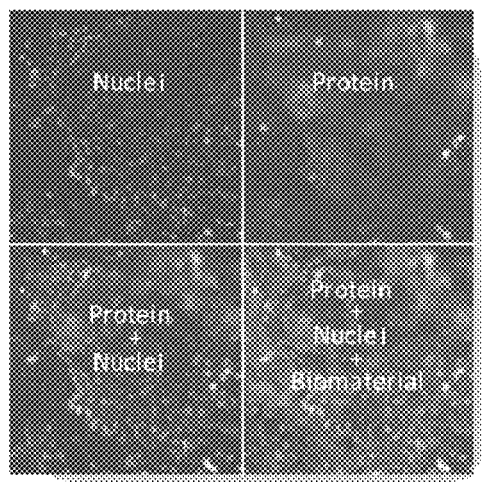
FIG. 24: Confocal microscopy images of the immunolabeling.
Figure 25:
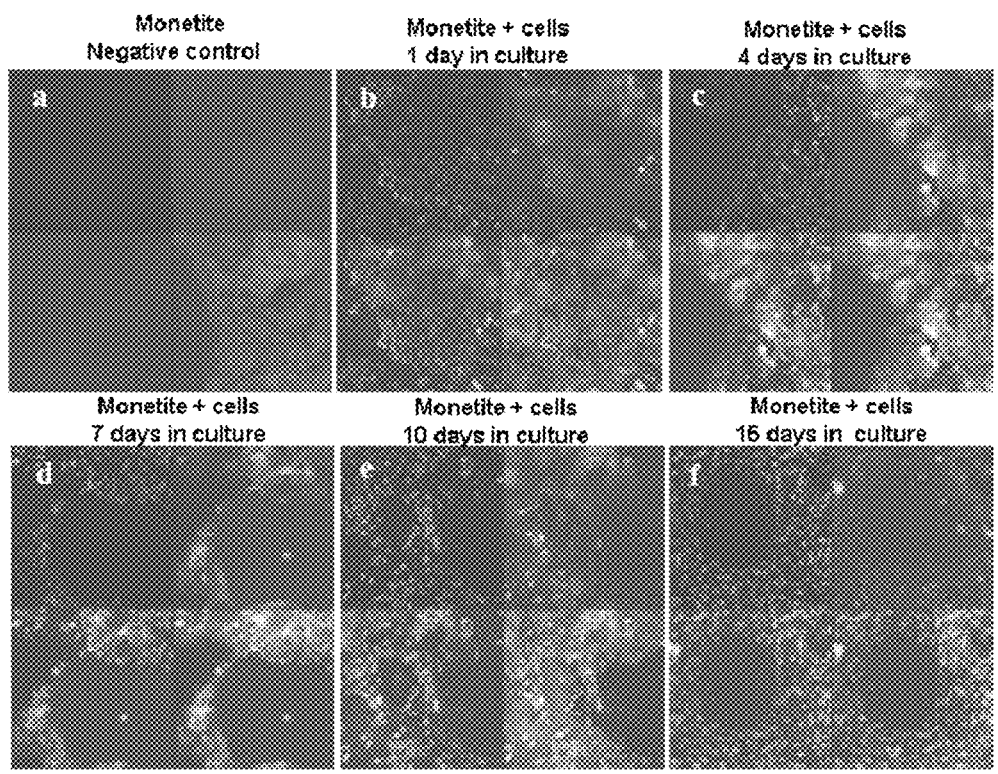
In FIGS. 25-31, each of Figures a-f are also subdivided into the mentioned quadrants, the indicated information having to be interpreted in each of them.
Figure 26:
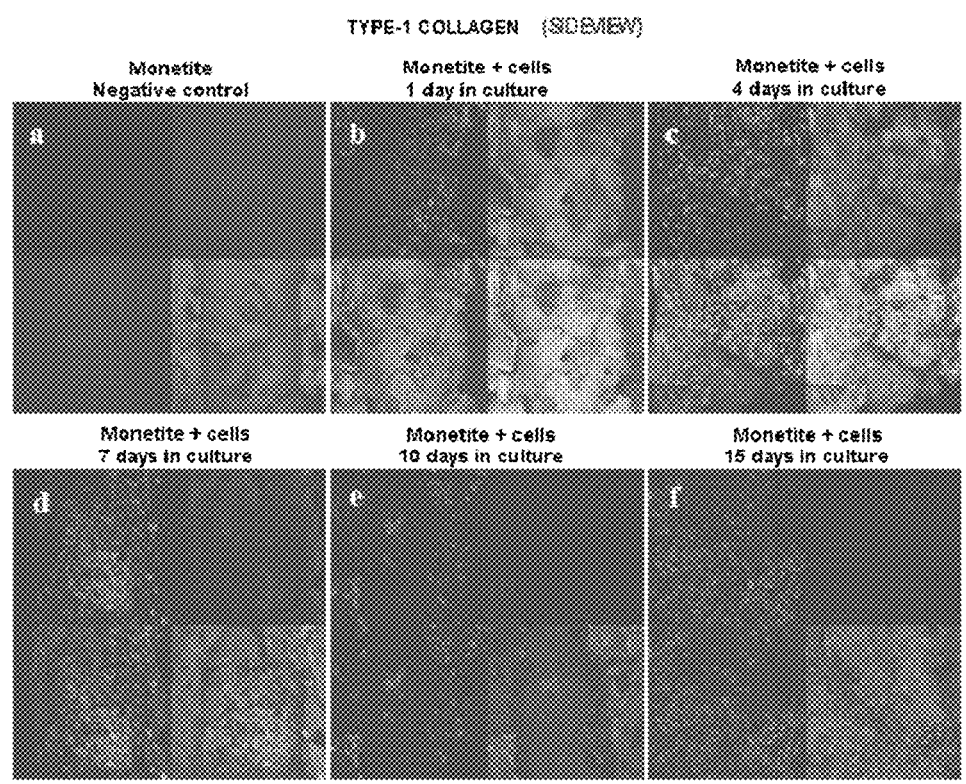

The predifferentiated cells still show the same expression pattern of the genes related to bone regeneration as the undifferentiated AMSCs. When the predifferentiated AMSCs are arranged in the biomaterial, the expression of these genes is maintained, no signs of interaction decreasing the expression of genes involved in bone regeneration being shown (FIG. 23).

The low expression of the enzyme alkaline phosphatase can be due to the fact that this enzyme is preferably not involved in the initial phases of the formation of the osteoid matrix. At the start of the bone formation, the synthesis and excretion of proteins into the matrix first occur; these proteins form an ordered structure in which the calcium salts will be deposited. Alkaline phosphatase is involved at the end of the process when mineralization occurs. This enzyme generates phosphate ions (which in this case are already being provided by the biomaterial) and the increase of the concentration of these ions in the matrix creates nucleation centers for the deposition of mineral salts.

Thus, as a final conclusion it should be indicated that the structured Monetite biomaterial of the invention, unlike the amorphous Monetite biomaterial, allows a complete colonization of both its external and its internal structure by the cells, the arrival of nutrients and gases to the entire structure to maintain high viability profiles and an induction of proliferation, as well as a higher expression of the genes related to osteosynthesis and the generation of new bone matrix.

Example 8

Analysis of the Secretion of Extracellular Matrix in the Biomaterial with Structured Porosity by the Cells Over Time. Potency 8.1 Study of the Expression of the Proteins Involved in the Formation of the extracellular matrix over time (OPN, OCA, Type-1 Collagen).

Bone is a highly vascularized mineralized conjunctive tissue containing specialized cells, organic matrix formed by proteins and mineral phase formed by calcium salts. The protein matrix allows it to be flexible and tolerate stress, whereas the calcium salts provide it with firmness and resistance to pressure. In the bone formation process, the components of the protein matrix are synthesized first, forming an ordered structure in which the calcium salts will subsequently be deposited.

The protein matrix represents a third of the bone weight. It is formed by proteins such as type-I collagen (>95%) and others involved in the fixing of calcium, such as osteocalcin (OCA-15%) and osteopontin (OPN). Collagen-I and OPN are expressed in an early manner in osteoprogenitor cells. OCA appears when mineralization starts and is a useful marker for final stages of osteoblast differentiation. The predifferentiated cells synthesize type-1 collagen, osteopontin and osteocalcin in their cytoplasm as occurs in bone cells. It has also been demonstrated that the predifferentiated cells express the OPN, OCA and type-1 collagen genes when they are arranged on the matrices of monetite with structured porosity of the invention. It is therefore important to determine if these cells, in addition to expressing their genes, are capable of synthesizing these proteins and excreting them to form the ordered structure in the matrix, essential for the deposition of calcium salts in the formation of the new bone.

The following process was carried out:
Arrangement of 300,000 predifferentiated AMSCs per cm$^2$ of the biomaterial.
Immunodetection of the extracellular bone matrix proteins OPN, OCA and COL-1 in the biomaterial.
Analysis by means of confocal microscopy at the times 1, 4, 7, 10 and 15 days of association with the biomaterial.
As on previous occasions, TOPVIEW images (FIGS. 25, 27, 29 and 31*a*) of the surface of the biomaterial and SIDEVIEW images (FIGS. 26, 28, 30 and 31*b*) corresponding to longitudinal section reconstructions of the interior of the pore are presented.

The interpretation of the immunolabeling images (FIGS. 25 and 26) indicate the formation and secretion of Collagen I from the first day of association, which increases as time goes by. An increase of the number of cells in the biomaterial from day 1 to day 15 is also observed, which corroborates the capacity of the AMSCs to colonize the biomaterial with structured porosity, as has been determined in previous experiments.

In the SIDEVIEW images (FIG. 26), collagen labeling is not observed after day 7 of association, which is due to the obturation which occurs in the pores, as has been observed in the SEM images (FIGS. 17-18 and 20-21), which prevents the diffusion of the antibody into the biomaterial. This phenomenon occurs in all the immunolabelings performed, after day 7 of association.

Figure 27:
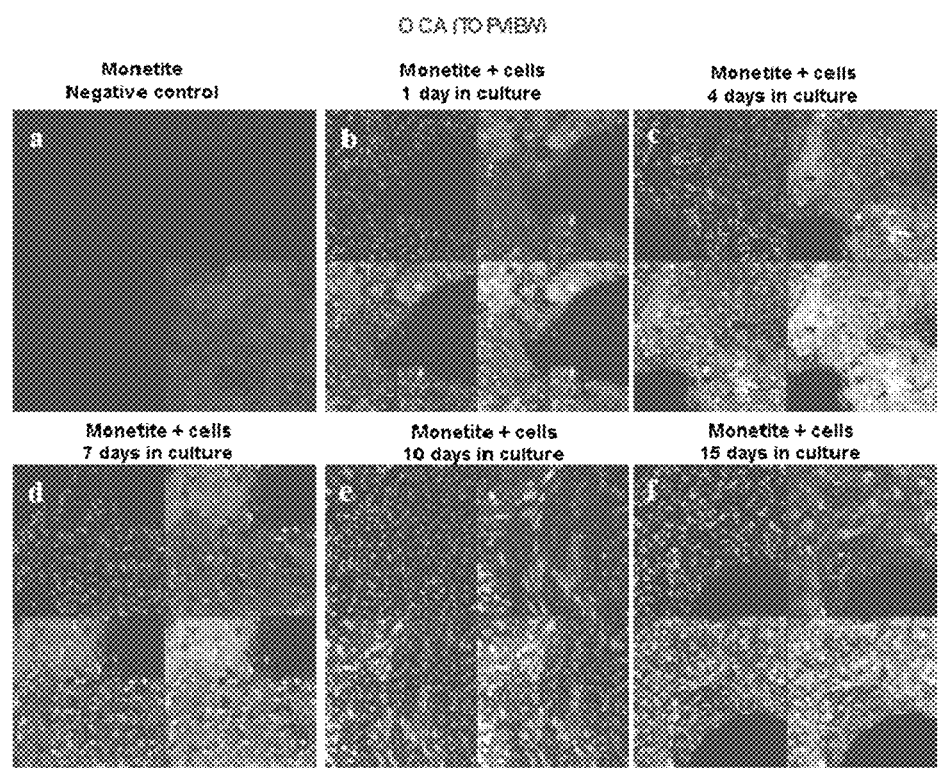
Figure 28:
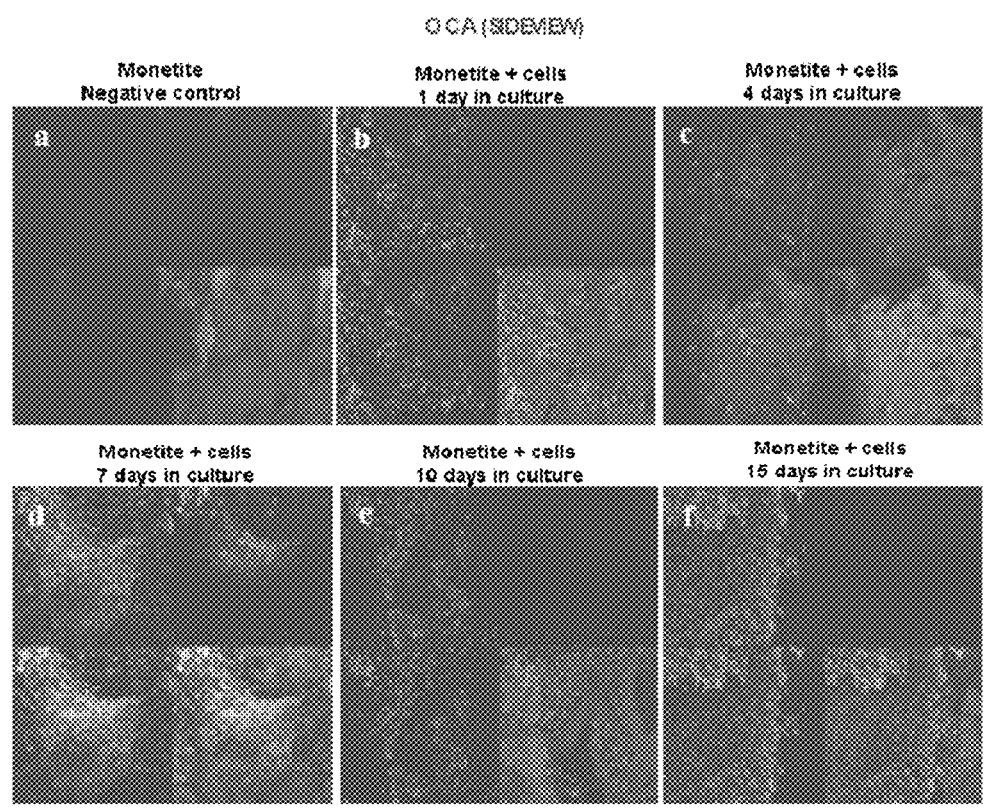
Figure 29:
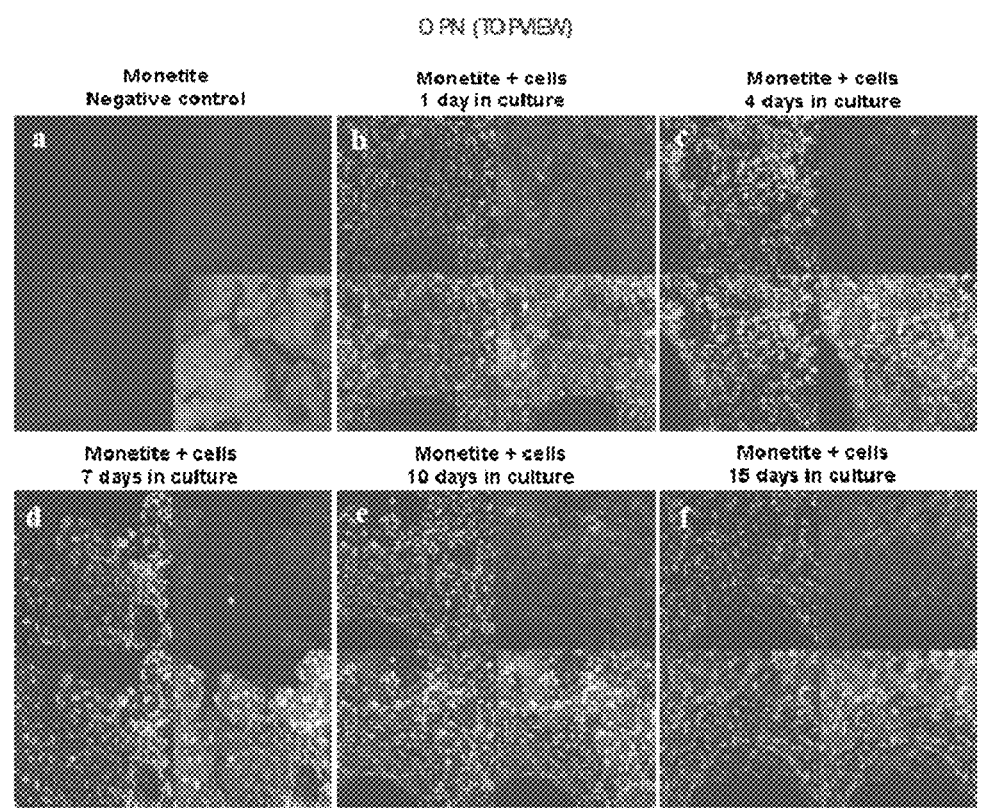
Figure 30:
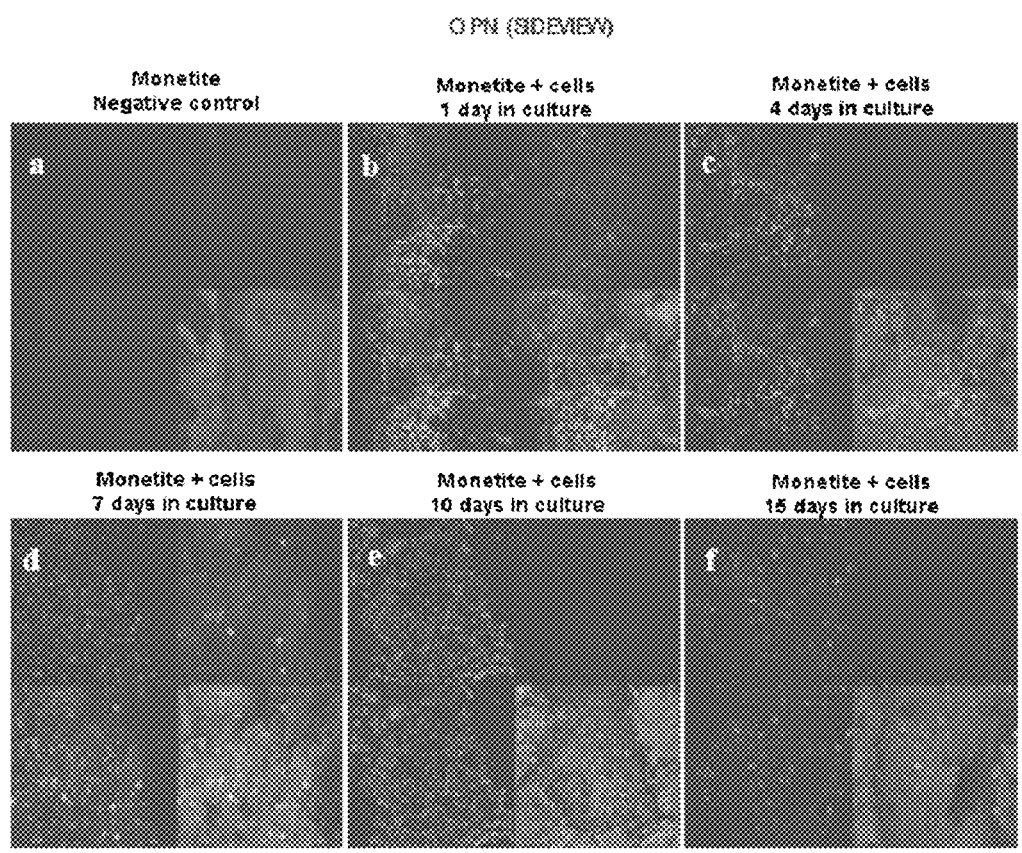

In relation to Osteocalcin, the predifferentiated AMSCs produce and secrete OCA in the biomaterial in an increasing manner as the association time goes by. The images of the internal area of the pores only show labeling up to 7 days, again due to the obturation of the pores and the difficulty in the diffusion of the antibody. However, these images allow observing a high colonization of the nuclei as the culture time in the biomaterial goes by, in the entire length of the pore (FIGS. 27 and 28).

In the case of osteopontin (OPN) (FIGS. 29 and 30), a synthesis and excretion of the protein in the biomaterial are also observed from day 1 to day 15 of association. Again, the images of the interior of the pores (FIG. 30) are poorer due to the difficulty in the diffusion of the antibody.

To corroborate that the lack of signal in the longitudinal interior of the pores over time is due to the difficulty in the diffusion of the antibody, the immunolabeling of the proteins was carried out after fracturing the biomaterial such that the wall of the internal pore is completely exposed, thus there is direct access to the entire internal surface of the pores (FIGS. 26, 28, 30 and 31*b*).

Figure 31:
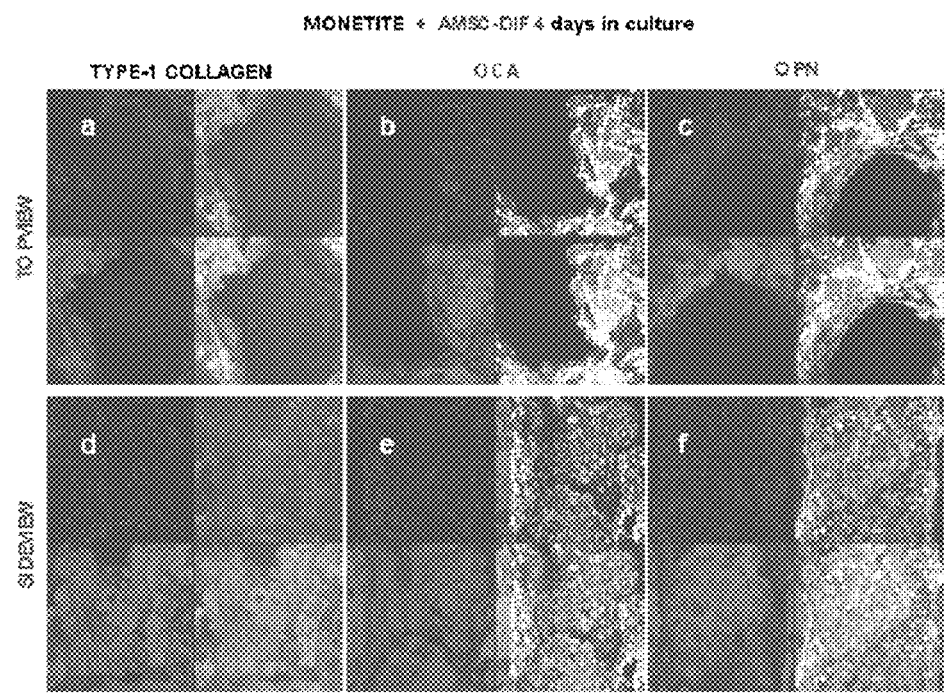

As can be observed in FIG. 31, at 4 days, the possible association time of the biomaterial of the invention prior to performing the implantation in the patient, a pronounced labeling of all the analyzed proteins both in the surface of the biomaterial of the invention and in the entire length of the internal surface of the pores is observed. These results indicate that the predifferentiated MSCs which are in the biomaterial with structured porosity are capable of synthesizing and secreting proteins related to bone synthesis such as type-I collagen, osteopontin and osteocalcin.

8.2 Analysis of the Calcium Synthesized by the Cells on the Biomaterial Over Time by Means of EDX.

It has been verified that the predifferentiated AMSCs in the biomaterial are capable of initiating the synthesis of proteins for the formation of new bone, but for a stable bone matrix to be produced it is furthermore necessary for a mineralization process to occur.

To determine this fact, it is analyzed if the AMSCs are capable of synthesizing calcium deposits to form the mineral phase of bone.

In the organism, the osteoblasts participate in the mineralization of the organic matrix, producing 100 nm matrix vesicles surrounded by membrane, in which $Ca^{2+}$ and $PO_4^{2-}$, rich in alkaline phosphatase and pyrophosphatase, enzymes capable of generating $PO_4^{2-}$ ions, accumulate. The increase of these ions induces the formation nucleation centers, necessary for the deposition of mineral salts.

One of the calcium-binding proteins is osteocalcin which, according to the results obtained, forms part of the organic matrix synthesized by the predifferentiated cells on the biomaterial. The high expression of this protein suggests that the cells can secrete calcium deposits to form the mineral of the new bone. It is therefore interesting to study if these cells can release calcium deposits into the extracellular medium. This calcium could form part of the new matrix, either forming hydroxyapatite crystals or binding to the proteins and being absorbed in the matrix as occurs in the organism.

The following process was carried out:
Arrangement of predifferentiated AMSCs on the biomaterial at the same concentration as in the previous experiments.

Maintenance in association for 4, 7, 10, and 15 days.
Analysis of the calcium by means of SEM associated to EDX (energy dispersion by means of X-rays). This technique allows analyzing and distinguishing chemical elements present in a sample.

Figure 32:
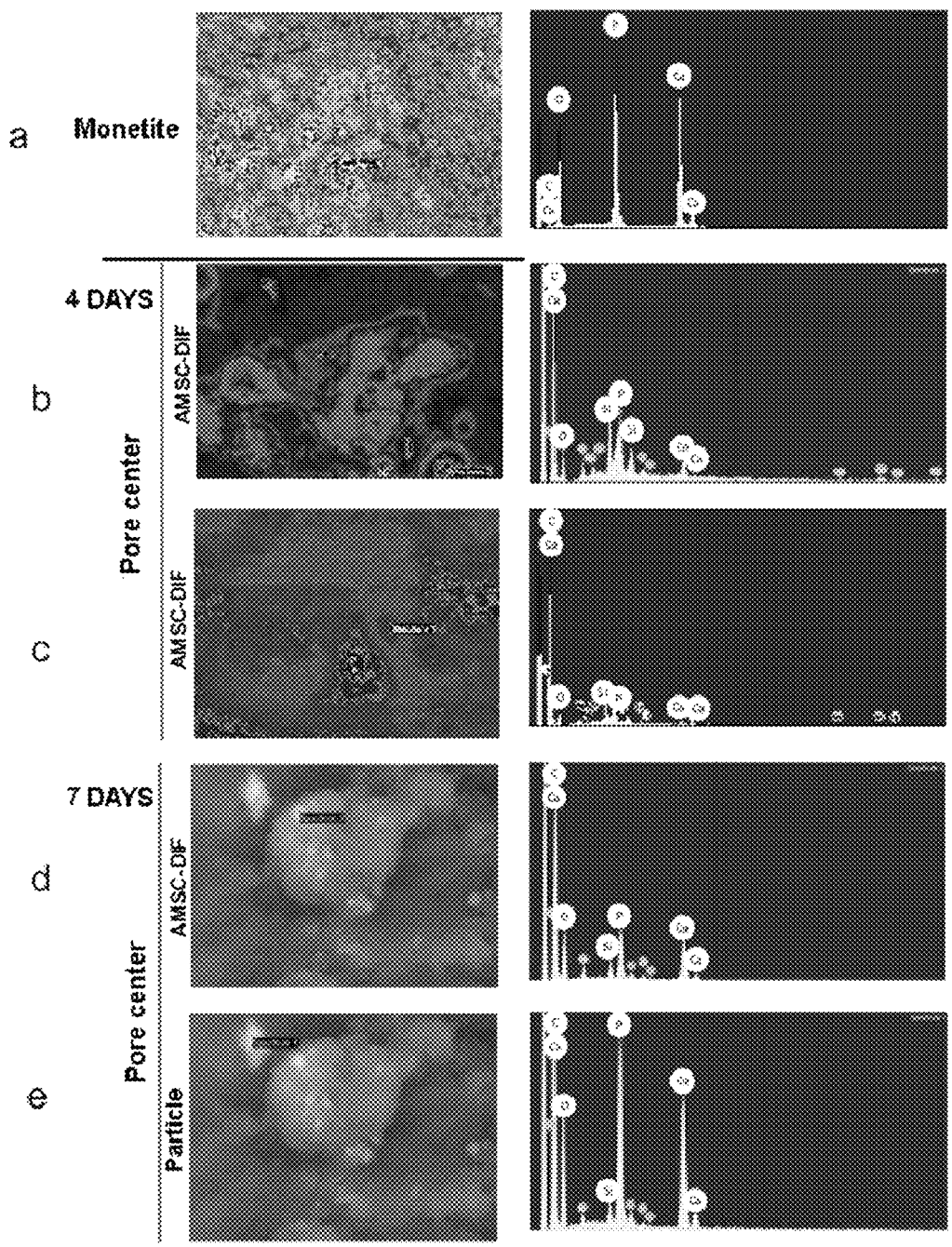
FIGS. 32 and 33: Analysis of essential elements by SEM-EDX of the biomaterial and the AMSCs associated with the Monetite with structured porosity of the invention for 4 and 7 days (FIG. 32) and 10 and 15 days (FIG. 33). The images of the left column refer to the isolated areas in the center of the channels based on which the analysis of the elements present in the cells has been performed (images of the right column). The graphs indicate a distribution of elements different from that found in the biomaterial. Thus, there is an increase of the synthesis of the particles (Calcium, phosphorus and silicon) by the cells over the time in association with the biomaterial with structured porosity of the invention. It is therefore concluded that the conditions suitable for the formation of the calcium salts necessary for the mineral phase of bone to be formed are met.
Figure 33:
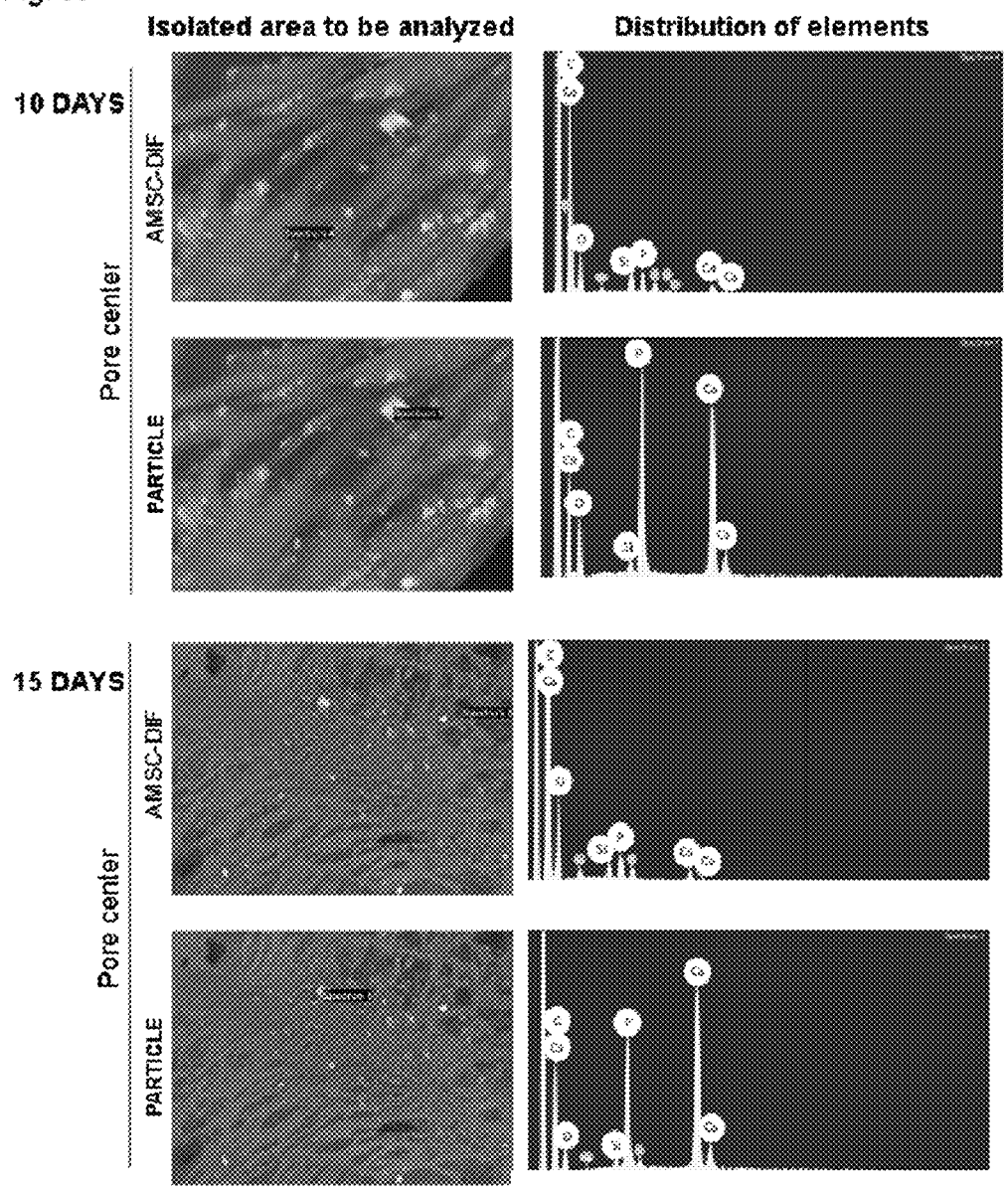

The images of the results obtained show isolated areas in which the distribution of elemental chemical elements has been analyzed by means of SEM-EDX (FIGS. 32 and 33). This technique allows determining the elements and their proportion in a sample using high definition. In this case it allows determining if the cells are producing elements related to the mineralization of the bone matrix.

The elements appearing in the biomaterial alone were first analyzed and a way to distinguish them from the bone matrix produced by the cells was sought, since the elements involved are the same (Ca and P).

The following elements are distinguished in the analysis of the biomaterial with structured porosity of the invention without AMSCs:
 3 calcium peaks emitting energy in three lines α, β and λ, depending on up to which energy level the incident electrons penetrate. The λ line overlaps with that of carbon and is more difficult to distinguish.
 Oxygen
 Phosphorus
 Carbon Analysis of the AMSCs in the Biomaterial with Structured Porosity of the Invention:

In order to be able to determine the elements present in the cells, without the interference of those of the biomaterial, points in the center of the channels far from the walls of the biomaterial have been taken as a reference, therefore the measurements and the elements detected correspond exclusively to the cells. Measurements have been taken at 4, 7, 10 and 15 days of association.

The graphs of FIGS. 32 and 33 indicate a distribution of elements different from the one found in the biomaterial. There is a completely different distribution of elements, including, as a novelty, silicon, a distinctive element coming from the cells, which does not appear in any sample taken in the biomaterial, and a very significant increase of Carbon. In other words, the following can be distinguished in the cells:
 Calcium in its 3 energy lines
 Oxygen
 Phosphorus
 Silicon
 Carbon At 4 days of association, electron-dense particles coming from the cells are still not observed. The distribution of the elements shows a pattern different from that of monetite, the calcium peaks are very low and there are other peaks such as those of silicon and other elements forming part of the cells. (FIGS. 32b and c)

At 7 days, particles that are more electron-dense are observed in the cells and the distribution of their elements is slightly different, especially in relation to the calcium peaks, which are more intense in the particles. (FIGS. 32d and e)

At 10 and 15 days of culture, it is observed that the cells completely occupy the center of the pore and that there are clearly electron-dense particles thereon, with very intense calcium and phosphorus peaks. When the chemical composition of the cells is analyzed, it gives a pattern of rather lower calcium lines than when the composition of the electron-dense particles is analyzed, both at 10 and at 15 days of the culture. (FIGS. 33 a-b and c-d)

Figure 34:
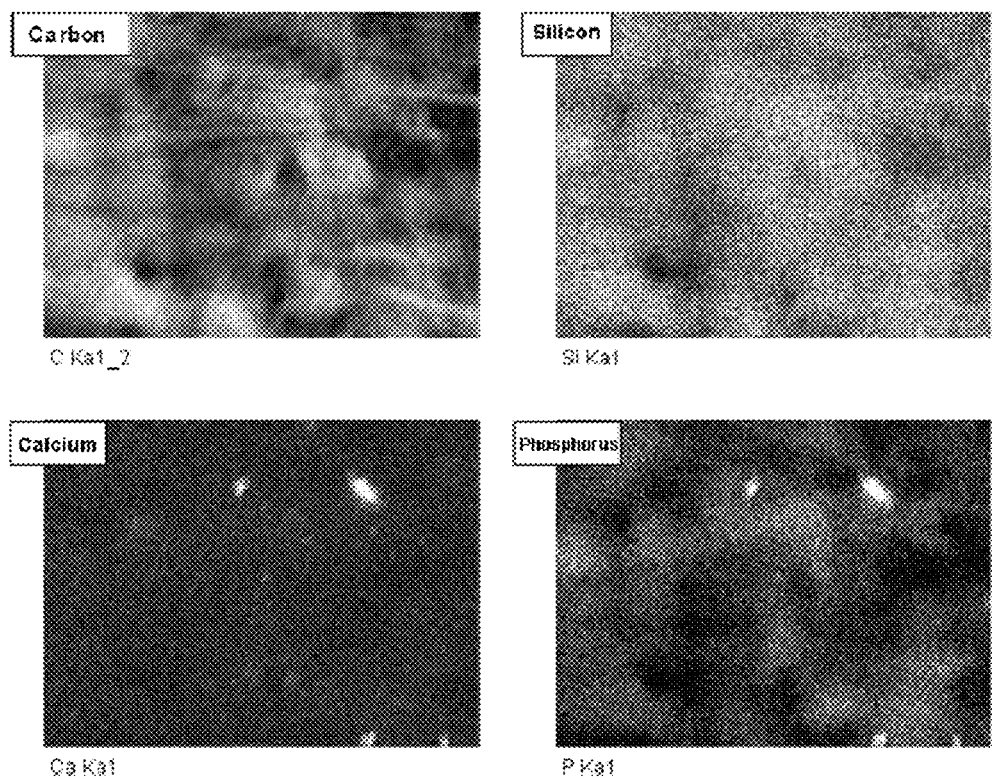
FIG. 34: SEM-EDX image which shows the distribution of the basic elements in an area in which only AMSCs are present. In the images of calcium and phosphorus, the electron-dense particles formed by the two elements can be seen (they are in the same location of the area).

According to the results obtained over the association time, electron-dense particles appear in an increasing manner, the main chemical composition of which is phosphorus and calcium (FIG. 34).

These electron-dense Calcium and Phosphorus particles are synthesized and excreted by the cells, since they appear associated with silicon (exclusive of the cells) and the measurement points have been taken in an area without biomaterial. These particles can be matrix vesicles which are present in the organism, in which $Ca^{2+}$ and $PO_4^{2-}$ accumulate. These elements are the ones which initiate the formation of the new mineralized bone matrix.

The fact that Silicon formed by the cells appears is very relevant as an indicator of the formation of new matrix and of the bone regeneration capacity. In the organism, the silicon is concentrated in the osteoblasts and is involved in the production of the matrix and in the deposition of mineral salts.

Studies carried out by Schwarz and Carliste demonstrate an important role of silicon in osteogenesis. According to these authors, silicon is presented at high levels in calcification sites. They demonstrate that in places in which an intense calcification process occurs, as is the case of fractures, there are considerable concentrations of silicon.

Silicon acts as an element which allows longitudinal bonds between the proteins and polysaccharides or between the polysaccharides. It is involved in the formation of the ordered protein structure in the matrix, so that correct bone mineralization is carried out.

In conclusion, the increase of the synthesis of the particles over the time in association with the biomaterial of monetite with structured porosity, formed by Calcium, Phosphorus and Silicon, indicates that the conditions suitable for the formation of the calcium salts necessary for the mineral phase of bone to be formed are met.

Example 9

Analysis of the Capacity of Autocrine Secretion of Growth Factors Related to Bone Regeneration by the Cells when They are Arranged in the Biomaterial of Monetite with Structured Porosity. Potency Growth factors are proteins produced by bone cells acting as cell function modulators. It is described in the literature that TGF-β1 is an important factor in bone remodeling since it is synthesized by osteoblasts, enhancing their differentiation and favoring the synthesis of osteoid matrix (Riancho et al., 2003). TGF-β1 has chemotactic effects on the precursors of osteoblasts, stimulating their proliferation and the synthesis of collagen (Fernandez-Tresguerres et al., 2006).

It is so involved in bone regeneration that it is being used as a prognostic marker in serology to determine the capacity that an individual may have to heal a complicated fracture (Zimmermann, 2005).

To determine the capacity of predifferentiated AMSCs to secrete this growth factor with or without monetite biomaterial with structured porosity, the soluble factor in the culture media is quantified. These media come from culturing predifferentiated cells alone or predifferentiated cells in contact with the biomaterial. The following process was carried out:
 Arrangement of different cell concentrations: 0.5-1-2-3-4-5 million predifferentiated cells in 6 cm$^2$ of surface and in a volume of 1.5 ml of medium. Culture for 7 days.
 Arrangement of 2×10$^6$ predifferentiated cells in 6 cm$^2$ of surface in a volume of 1.5 ml of culture medium for 1, 4, 7, 10 and 15 days of culture.
 ELISA Analysis of the amount of soluble TGF-β1.

The results show that in all the cases a relevant presence of the factor in the medium is observed (FIGS. 35-38). The detected concentrations vary depending on the moment of the cell metabolism and on the use being made of the factor in the cell.

Figure 35:
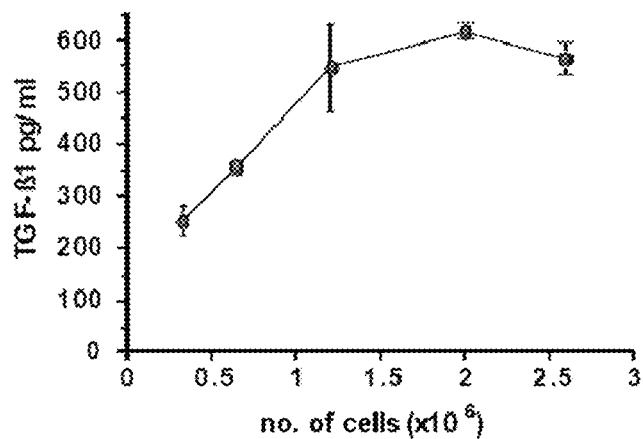
FIG. 35: Secretion of TGF-β1(pg/ml) obtained from different concentrations of predifferentiated cells growing without monetite for 7 days in culture. A gradual increase in the concentration of TGF-β1 (pg/ml) for lower cell concentrations and a slight decrease or destabilization for higher cell concentrations due to the negative feed-back mechanism of TGF-β1 are observed.

When the cells grow without the biomaterial with structured porosity, a gradual increase in the concentration of TGF-β1 is observed at the lower cell concentrations, proportional to the number of cells per surface (FIG. 35). At the higher concentrations, a slight decrease or stabilization is observed, which can be due to the fact that the factor is exerting its function bound to the recipient, to the fact that it has already fulfilled its function, to the fact that the high concentration is inhibiting its own synthesis by a feedback mechanism.

Figure 36:
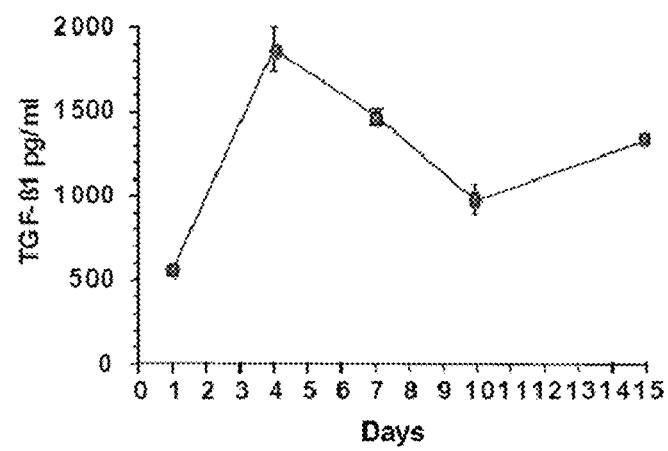
FIG. 36: Secretion of TGF-β1(pg/ml) obtained from the predifferentiated cells over the time in culture. $2 \times 10^6$ cells were seeded on a 6 cm$^2$ surface, the secretion is analyzed at different times in culture, observing a typical behavior of feedback mechanisms consisting of an increase of the synthesis and secretion of the mechanism followed by a decrease of the secretion until the start of a new increase in the secretion.

FIG. 36 shows the secretion of the growth factor of the predifferentiated cells over the time in culture. A peak in the synthesis and secretion into the medium is observed at 4 days of the culture, subsequently there is a decrease up to day 10, after which it initiates a new increase in the secretion.

This behavior is typical of the growth factors acting according to a feedback mechanism:
1: there is synthesis and secretion into the medium.
2: it binds to its specific recipient in the surface of the recipient cell to exert its function, at which time a decrease of its presence in the culture medium can be observed.
3: if it is still necessary for the activation of certain cell processes, it again starts its synthesis and secretion into the medium in order to maintain its effect until the cell determines the inhibition of its synthesis.

Figure 37:
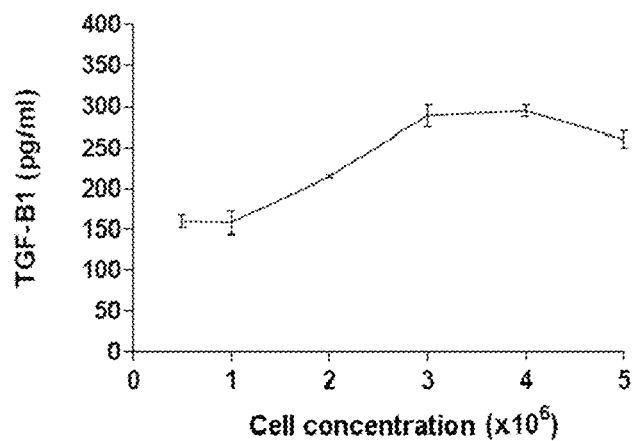
FIG. 37: Secretion of TGF-β1(pg/ml) obtained from different concentrations of predifferentiated cells growing on the biomaterial for 7 days in culture. It can be observed from this graph how the presence of the factor in the medium correlates with the increase of the number of cells in the biomaterial.

When the cells are arranged in the biomaterial, the results demonstrate that they are also capable of synthesizing and secreting the factor TGF-β1 into the culture medium (FIG. 37).

The presence of the factor in the medium correlates with the increase of the number of cells in the biomaterial, until there is again a stabilization of the secretion, which can be due to the fact that it is not necessary to increase the levels for its action.

Figure 38:
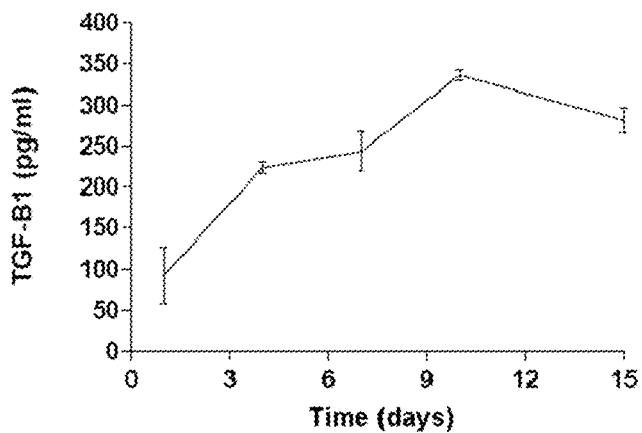
FIG. 38: Secretion of TGF-β1(pg/ml) obtained from the predifferentiated cells growing on the biomaterial over the time in culture. $2 \times 10^6$ cells were seeded on the biomaterials, the secretion is analyzed at different times in culture. It is inferred from the graph that there is an increase of the secretion from day 1 to day 10 of culture, after which time it starts to be stabilized and decrease moderately.

Likewise, one and the same cell concentration arranged on monetite with structured porosity over the time in culture increases the secretion of the factor, which can be related to the cell increase over time (FIG. 38). Specifically, the results show that there is an increase of the secretion from day 1 to day 10 of culture, after which time it starts to be stabilized and decrease moderately.

This increase may also not be related to an increase in the number of cells, but rather due to an induction to enhance the synthesis of extracellular matrix. After day 10 of association, its synthesis decreases or the factor is mostly bound to recipients exerting its function, not being observed in free form in the culture medium.

In this case, the feedback mechanism of the factor is regulated in a slightly different manner from that observed when the cells do not grow on the matrix of Monetite with structured porosity of the invention, such that the increase in the secretion is maintained up to day 10, decreasing after this day.

In conclusion, the predifferentiated cells growing on the monetite biomaterial with structured porosity are capable of synthesizing and secreting the factor TGF-β1 into the external medium. As has been demonstrated in the study of the gene expression of this factor, in the predifferentiated cells growing in the biomaterial, the expression of the factor remains constant over the time in culture except for day 7, on which a slightly lower expression was observed. Furthermore, the expression in the predifferentiated cells growing with and without biomaterial is similar. Therefore, it can be assumed that the different quantification of the factor in both cases is due to a difference in the rate of binding to the receptor and of transmission of the signal to the interior. Or perhaps the cells growing on the biomaterial have more receptors and the factor is mostly bound to them, which would entail an enhancement of the bone regeneration process, therefore the detection of the soluble factor is lower in these cases.

In short, the predifferentiated cells growing on the biomaterial of monetite with structured porosity of the invention synthesize and secrete TGF-β1 into the culture medium. This factor can favor the synthesis of osteoid matrix.

Example 10

In Vivo Comparison of the Matrices of Monetite with Structured Porosity of the Invention with Matrices of Brushite with Structured Porosity The structured Monetite biomaterial of the present invention has advantages over Brushite, since it is more stable and has a resorption rate which is more suitable and adapted to bone remodeling.

A study was performed to determine the resorption rate of the Monetite biomaterials with structured porosity and of Brushite biomaterials with the same porosity structure as those of the present invention by means of using a critical defect model in rabbit calvarial bone. Six rabbits of the New Zealand variety were included in the study, using 3 animals to analyze the capacity of reabsorption of each biomaterial. To that end, exposure to the rabbit cranium was carried out by means of a sagittal incision of the scalp. The periosteum was then carefully dissected, bicortical defects of 1 cm in diameter were prepared. In each animal, the biomaterials were arranged in one of the defects, leaving the contralateral one as a control. The surgical area was generously irrigated and the periosteum, the subcutaneous tissues and scalp were sutured using the suitable surgical techniques.

After 4, 8 and 12 weeks from the implantation, the animals were sacrificed and the implanted parts were collected for their histomorphometric analysis. The most suitable time for the total resorption of a biomaterial used to induce bone regeneration in humans is estimated at between 6 to 18 months. This resorption rate is important since if the biomaterial is very soluble and the degradation is too quick, the osteoblasts lose the scaffolding which will allow them to be maintained and produce and place new bone matrix, however, if the biomaterial used is too stable, the osteoclasts will not be able to produce a degradation synchronized with the formation of new bone by the osteoblasts. For this reason, it is necessary to apply a biomaterial the degradation of which allows bone remodeling and, furthermore, for the ions and degradation products to not cause significant alterations in the pH of the environment and in the osteogenic cells. In this case, the results show that the implantation area did not show signs of inflammation with any of the biomaterials used. With both biomaterials, the histological study already showed the formation of new bone from week 4, as well as the first signs of resorption (perforations in the biomaterials, osteoclast clustering areas). However, although it is observed that Brushite has been mostly resorbed at 12 weeks of implantation, Monetite material can still be observed, which provides more stability to the bone regeneration process and more coupling with the bone remodeling phase. The increase of the resorption time of the Monetite biomaterial of the invention will give rise to the formation of more bone mass since the osteoblasts will have more time for the formation and deposition of new mineralized bone matrix.

Thus, it can be concluded that the resorption rate of Monetite is more adjusted to bone remodeling, maintaining for more time the suitable scaffolding for the colonization of the osteoblasts and for the synthesis of new bone matrix, without the risk of formation into Hydroxyapatite, due to a too high resorption rate, as may occur in the case of Brushite.

Example 11

Comparison of a Particular Embodiment of the Matrix of Monetite with Structured Porosity of the Invention With a Matrix of Monetite with a Different Porosity Structure The biomaterial developed in the present invention has characteristics which are especially relevant for achieving effective bone regeneration, including a homogeneously distributed microporosity and macroporosity, and the application thereof in the form of an assembly of parts, which will allow a better adaptation to the bone defect, a homogeneous entrance of nutrients, gases and cells in the entire area to be repaired, such that necrotic areas are not produced.

To study the advantage of the biomaterial of the invention and its form of application, the regenerative capacity of the pellets of the invention of 5 mm in diameter, 3 mm in height and 12 macropores of 0.5 mm in diameter separated from one another by 0.5 mm was compared with respect to a Monetite biomaterial having the porosity structure of Example 1 of patent application U.S. Pat. No. 6,605,516. Said matrix corresponds to a cylinder of 10 mm in diameter by 10 mm in height, having a central channel of 2 mm in diameter and a hexagonal network of 60 cylindrical pores of 0.5 mm in diameter, parallel to the central macropore of 2 mm, and separated from one another by a distance of 1 mm. Thus, said matrix does not have a homogeneous pore diameter control and must be applied in a single part, such that the complete size is adjusted to the bone defect.

An analysis of the formation of new bone and vascularization in the implantation area of the two types of biomaterials was carried out. For the in vivo experimentation, 6 sheep were used in which a critical defect in the tibia and a stabilization by osteosynthesis techniques were performed. In the created defect, an assembly of parts of the monetite biomaterial with structured porosity of the invention was applied in 3 of them and a single part of biomaterial adjusted to the size of the defect was applied in the other 3, leaving in all of them the adjacent leg as a control (with formation of the critical defect and stabilization of the fracture but without filling of biomaterial). Before the implantation of the biomaterials, the latter were seeded with an identical number of mesenchymal stem cells from the adipose tissue obtained from the sheep.

The analysis of the new bone tissue formed and the resorption of both types of biomaterials was performed by means of a continuous radiographic control and a histological study at 3 and 6 months of the implantation. The serial X-rays allow observing a complete integration of the biomaterial with structured porosity of the invention in the implant area, as well as an active resorption of said biomaterial, which still persists at 6 months, since its degradation rate is adjusted to bone remodeling with this design. At radiographic level, changes are not observed in the biomaterial arranged as a single block in the implanted area. The histomorphometric analysis allowed confirming at 3 months of the implantation a colonization of bone osteoblasts and osteoclasts in the entire structure of the monetite biomaterial with structured porosity of the invention, and the homogeneous formation of new bone, with a complete integration thereof at 6 months with an incipient vascular network which will allow the survival of the new tissue formed without the formation of necrotic areas. However, inside the single block, virtually all the new tissue formed is restricted to the area peripheral to the implant, its internal area remaining with a significant lower colonization of the cells of the adjacent tissue and without signs of formation of new blood vessels. The homogeneous distribution of the pores with a diameter of 500 μM and a separation therebetween of also 500 μM in the biomaterial causes a large surface of contact both in the surface area and inside the biomaterial of the invention, which improves the capacity of interaction with the tissue of the damaged area, areas of activity in terms of the generation of new bone being produced in all the areas of the biomaterial simultaneously.

These results allow concluding that the recipient tissue of the implantation interacts in a significantly more suitable manner with the biomaterial of the invention to give rise to the homogeneous formation of new vascularized bone tissue. However, the use of a single block of Monetite of Example 1 of patent application U.S. Pat. No. 6,605,516 hinders the interrelation and integration in the area of the bone defect. The formation of new bone and the cell colonization therein are significantly lower even at 6 months of the implantation.

In addition, on most occasions the bone defects in the patients do not form perfect shapes, as occurs when these defects are induced in sheep as part of an experimental study. The bone defects are very different and the edges of the fracture are very irregular on a number of occasions. In some cases, the space formed by the bone defect is very limited, as occurs for example in hypertrophic pseudarthrosis, therefore introducing a single preformed block which is coupled in the area is very complicated and is not capable of molding to a deformed area. The use of the design of the invention, an assembly of small-sized parts of Monetite biomaterial with a homogeneous structuring of macropores allows the adaptation thereof to complicated bone defects with different shapes and dimensions, such that the affected area is completely exposed to the biomaterial and to the supplied cells to activate the healing process.

LITERATURE

Chow L C, Markovic M, Takagi S. 2003. A dual constant composition titration system as an in vivo resorption model for comparing dissolution rates of calcium phosphate biomaterials. J Biomed Mater Res B: Appl Biomater 65: 245-251.

Constanz B R, Barr B M, Ison I C, Fulmer M T, Baker J, Mckinney L, Goodman S B, Gunasekaren S, Delaney D C, Ross J, Poser R D. 1998. Histological, chemical, and crystallographic analysis of four calcium phosphate cements in different rabbit osseous sites. J Biomed Mater Res B: appl Biomater 43: 451-461.

De Boever A L & De Boever J A. 2005. Guided bone regeneration around nonsubmerged implants in narrow alveolar ridges: a prospective long-term clinical study. Clinical Oral Implants Research 16: 549-556.

Eggli P S, Muller W, Schenk R K. 1988. Porous Hydroxyapatite and tricalcium phosphate cylinders with two different pore size ranges implanted in the cancellous bone of rabbits. A comparative histomorphometric and histologic study of bone ingrowth and implant substitution. Clin Orthop 232: 127-138.

Fernandez-Tresguerres I, Alobera M A, del Canto M, Blanco L. Bases fisiológicas de la regeneración ósea II. El proceso de remodelado. Med. oral patol. oral cir. bucal (Internet) v.11 n.2 Madrid mar.-5 abr. 2006.

Tamimi F M, Torres J, Tresguerres I, Clemente C, Lopez Cabarcos E, Blanco L J. Bone augmentation in rabbit calvariae: comparative study between Bio-Oss and a novel β-TCP/DCPD granulate. J Clin Periodontol 2006; 33: 922-928. 2006.

Franco J, Souto A, Rey P, Uitian F, Martinez Insua A. 2006. Procesamiento cerámico de B-TCP para la fabricación de piezas implantables. Bol. Soc. Esp. Ceram. V., 45 (4) 265-270.

Gimeno M D. Sustitutivos óseos en fracturas del radio distal. Patología del Aparato Locomotor, 2007; 5 Supl. II: 82-90. Frayssinel P, Vidalain J P, Rauz X, Cartillier J C, Rouquet N. 1999. Hydroxyapatite particle migration. European journal of Orthopaedic surgery & traumatology (9) 2: 95-98.

Gbureck U, Holzel T, Klammert U, Wurzler K, Muller F A, Barralet J E. Resorbable dicalcium phosphate bone substitutes made by 3D powder printing. Adv Funct Mater 2007; 17: 3940-5. Herron S, Thordarson D B, Winet H, Luk A, Bao J Y. 2003. Ingrowth of bone into absorbable bone cement: An in vivo microscopic evaluation. Am J Orthop 12: 581-584.

Riancho J A, Gutierrez G E. Factores reguladores de la resorción ósea. Rev Metab Oseo Min 2003; 1(2): 51-66. Schnettler R, Stahl P J, Alt V, Pavlidid T, Dingledein E, Wenish S. 2004. Calcium Phosphate-Based bone Substitutes. Eur J Trauma 30: 219-229.

Schwarz K. Significance and functions of silicon in warm-blooded animals. Review and Outlook. Biochemistry of Silicon and Related Problems. Plenum. New York. 1977: 207-230. Carlisle E M. Silicon. Handbook of nutritionally essential mineral elements. Dekker. New York. 1997: 603-618.

Suba Z, Takacs D, Gyulai-Gaal S, Kovacs K. 2004. Facilitation of beta-tricalcium phosphate-induced alveolar bone regeneration by platelet-rich plasma in beagle dogs: a histologic and histomorphometric study. International Journal of oral and Maxillofacial Implants 19: 832-838.

Sugawara A, Fujikawwa K, Takagi S, Chow L C, Nishiyama M, Murai S. Histopathological and cell enzyme studies of calcium phosphate cements. Dent Mater J 2004; 23: 613-620. Stubbs D, Deakin P, Chapman-5 Sheath P, Bruce J, Debes W, Gillies R M, Walha W R. 2004. In vivo evaluation of resorbable bone graft substitutes in a rabbit tibial defect model. Biomaterials 25: 5037-5044.

Takahashi Y, Tabata Y. (2004). Effect of the fiber diameter and porosity of nonwoven PET fabrics on the osteogenic differentiation of mesenchymal stem cells. J Biomater Sci Polym Ed 15 (1): 41-57.

Tamini F M, Torres J, Tresguerres I, Blanco L, Lopez-Cabarcos E. 2006. Vertical bone augmentation with granulated brushite cement set in glycolic acid. Int J Biomed Mater Res 80a: 1-10.

Tamini F M, Torres J, Tresguerres I, Clemente C, Lopez-Cabarcos E, Blanco L J. 2006. Bone augmentation in rabbit calvariae: comparative study between Bio-OssR and a novel B-TCP/DCPD granulate. J Clin Periodontol 33: 922-928.

Tas C & Bhaduri S B. 2004. Chemical processing of cahpo.2H2o: its conversion of hydroxyapatite. Journal of American Ceramic Society 87: 2195-2200.

Taylor J C, Cuff S E, Leger J P, Morra A, Anderson G I. 2002. In vitro osteoclast resorption of bone substitute biomaterials used for implant site augmentation: a pilot study. International Journal of Oral and Maxillofacial Implants 17: 321-330.

Trisi P, Rao W, Rebaudi A, Fiore P. 2003. Histologic effect of pure-phase betatricalcium phosphate on bone regeneration in human artificial jawbone defects. International Journal of periodontics restorative Dentistry 23: 69-77.

Wiltfang J, Schlegel K A, Schultze S, Nkenke E, Zimmermann R, Kessler P. Sinus floor augmentation with beta-tricalciumphosphate (beta-TCP): does platelet-rich plasma promote its osseus integration and degradation? Clin Oral Implants 2003 April; 14 (2): 213-8. 64

G. Zimmermann, P. Henle, M. Kusswetter, A. Moghaddam, A. Wentzensen, W. Richter, S. Weiss. TGF-β1 as a marker of delayed fracture healing. Bone, 2005 (36): 779-785.

The invention claimed is:

1. A composition for bone structure regeneration, wherein said composition comprises a plurality of three-dimensional matrices of monetite with structured porosity, wherein said matrices contain vertical cylindrical channels which longitudinally traverse each matrix from one end to the other, wherein all of the channels that longitudinally traverse each matrix are uniformly-sized cylindrical macropores that are uniformly separated from one another by 0.5 mm ±60µm, said macropores having a diameter of 500µm ±60µm, and wherein in each matrix, none of said cylindrical macropores are connected to each other via another macropore contained within said matrix;
   wherein said matrices are cylinders with a base diameter between 2 and 15 mm and a height between 1 and 5 mm, and have a perimetric area from said cylinder edge towards the center thereof of at least 0.5 mm which is free of macropores.

2. The composition of claim 1, wherein the monetite content of the matrices is at least 90%.

3. The composition of claim 2, wherein the monetite content of the matrices is 95%.

4. The composition of claim 2, wherein the monetite content of the matrices is 100%.

5. The composition of claim 1, wherein said matrices are obtained by heat-transforming a precursor material.

6. The composition of claim 5, wherein the precursor material which is heat-transformed into monetite consists of a mixture of a solid phase formed by basic calcium phosphates, acidic calcium phosphates, a pore-inducing agent and a retarder which is set by adding distilled water.

7. The composition of claim 6, wherein the molar ratio of basic phosphate/acidic phosphate is 1.6-1.8, the concentration of pore-inducing agent is 1-20% by weight, that of retarder is between 0.4-0.6% by weight and the (P/L) powder-liquid ratio of the monetite matrix is 3.

8. The composition of claim 7, wherein the molar ratio of basic phosphate/acidic phosphate is 1.785, the concentration of pore-inducing agent is 3-10% by weight and that of retarder is 0.54% by weight.

9. The composition of claim 5, wherein the acidic calcium phosphate is monocalcium phosphate, the basic calcium phosphate is beta-tricalcium phosphate, the pore-inducing agent is calcium carbonate and the retarder is sodium pyrophosphate.

10. The composition of claim 5, wherein the precursor material is Brushite.

11. The composition of claim 1, wherein said three-dimensional matrices are obtained from Brushite.

12. The composition of claim 11, wherein said matrices are cylinders with a base diameter of 10 mm, a height of 5 mm, and 64 cylindrical macropores, respecting a perimetric area of 0.5 mm from said cylinder edge towards the center thereof which is free of macropores.

13. The composition of claim 11, wherein said matrices are cylinders with a base diameter of 10 mm, a height of 3 mm, and 64 cylindrical macropores, respecting a perimetric area of 0.5 mm from said cylinder edge towards the center thereof which is free of macropores.

14. The composition of claim 11, wherein said matrices are cylinders with a base diameter of 8 mm, a height of 5 mm, and 39 cylindrical macropores, respecting a perimetric area of 0.5 mm from said cylinder edge towards the center thereof which is free of macropores.

15. The composition of claim 11, wherein said matrices are cylinders with a base diameter of 8 mm, a height of 3 mm, and 39 cylindrical macropores, respecting a perimetric area of 0.5 mm from said cylinder edge towards the center thereof which is free of macropores.

16. The composition of claim 11, wherein said matrices are cylinders with a base diameter of 7 mm, a height of 5 mm, and 28 cylindrical macropores, respecting a perimetric area of 0.5 mm from said cylinder edge towards the center thereof which is free of macropores.

17. The composition of claim 11, wherein said matrices are cylinders with a base diameter of 7 mm, a height of 3 mm, and 28 cylindrical macropores, respecting a perimetric area of 0.5 mm from said cylinder edge towards the center thereof which is free of macropores.

18. The composition of claim 11, wherein said matrices are cylinders with a base diameter of 5 mm, a height of 3 mm, and 12 cylindrical macropores, respecting a perimetric area of 0.5 mm from said cylinder edge towards center thereof which is free of macropores.

19. The composition of claim 1, wherein said matrices further comprise cells.

20. The composition of claim 19, wherein said cells are mesenchymal cells, osteoblasts, osteoclasts, osteocytes, endothelial cells or combinations thereof.

\* \* \* \* \*